United States Patent
Ootake et al.

(10) Patent No.: US 6,524,715 B1
(45) Date of Patent: Feb. 25, 2003

(54) THIN-FILM FORMING CHEMICAL ADSORPTION MATERIAL, PRODUCING METHOD THEREOF AND APPLICATIONS THEREOF

(75) Inventors: Tadashi Ootake, Neyagawa (JP); Kazufumi Ogawa, Nara (JP); Takaiki Nomura, Katano (JP); Takako Takebe, Katano (JP)

(73) Assignee: Matsushita Electric Industrial Co., Ltd. (JP)

( * ) Notice: Subject to any disclaimer, the term of this patent is extended or adjusted under 35 U.S.C. 154(b) by 154 days.

(21) Appl. No.: 09/786,158

(22) PCT Filed: Jul. 5, 2000

(86) PCT No.: PCT/JP00/04505

§ 371 (c)(1),
(2), (4) Date: Mar. 1, 2001

(87) PCT Pub. No.: WO01/02510

PCT Pub. Date: Jan. 11, 2001

(30) Foreign Application Priority Data

Jul. 5, 1999 (JP) ............................................. 11-190385
Jul. 5, 1999 (JP) ............................................. 11-190437

(51) Int. Cl.$^7$ ................................................. B32B 9/04
(52) U.S. Cl. ...................... 428/447; 428/421; 556/436; 556/465; 556/471; 556/466; 556/484
(58) Field of Search .................................. 428/447, 421; 556/436, 465, 471, 466, 484; 558/39; 570/101

(56) References Cited

U.S. PATENT DOCUMENTS 5,473,455 A   12/1995   Koike et al. .................. 359/76
5,604,615 A   2/1997    Iwagoe et al. ............... 349/124

FOREIGN PATENT DOCUMENTS

| EP | 0 962 460 A1 | 12/1999 |
| EP | 1 040 876 A1 | 10/2000 |
| EP | 1 067 132 A2 | 1/2001 |
| JP | 03-7913 | 1/1991 |
| JP | 07-72483 | 3/1995 |
| JP | 11-125822 | 5/1999 |
| JP | 2000-53684 | 2/2000 |
| JP | 2000-56309 | 2/2000 |

*Primary Examiner*—Harold Pyon
*Assistant Examiner*—Jane Rhee
(74) *Attorney, Agent, or Firm*—Parkhurst & Wendel, L.L.P.

(57) ABSTRACT

A thin film forming chemical absorption material including at least a functional group of the formula $CF_3$—$CF_2$—$CH_2$—O—(benzene)—CH=CH—C(O)—(benzene)— and a —SiX group (X represents halogen) as an end group bonded by siloxane bond. The chemical absorption material can form a monomolecular thin-film having photosensitive groups that are transparent and stable in a visible light region and cause photochemical reaction in an ultraviolet region. A liquid crystal alignment film includes an aggregation of adsorption molecules chemically absorbed directly on a surface with electrodes or chemically adsorbed indirectly thereon through another material layer having a characteristic group the formula above and a —O—Si bond group at a molecular end group. The liquid crystal alignment film is uniformly and strongly anchored on the substrate, has excellent thermal alignment stability, alignment controllability, and a film thickness permitting formation with good productivity.

57 Claims, 8 Drawing Sheets

Chemical Shift / PPM and to a producing method thereof. Also, the present invention relates to an organic thin film formed by use of the thin film forming chemical adsorption material and to a producing method thereof. Further, the present invention relates to a liquid crystal alignment film and to a producing method thereof. Furthermore, the present invention relate to a liquid crystal display using the same and to a producing method thereof and, further particularly, to a liquid crystal alignment film for use in a plane display panel using liquid crystals to display television (TV) picture, computer picture and the like, to a producing method thereof, and to a liquid crystal display device using it.

THIN-FILM FORMING CHEMICAL ADSORPTION MATERIAL, PRODUCING METHOD THEREOF AND APPLICATIONS THEREOF

TECHNICAL FIELD

The present invention relates to a chemical adsorption material to be chemically adsorbed on a surface of a substrate to form a thin film thereon and to a producing method thereof. More particularly, the present invention relates to a chemical adsorption material used mainly as liquid crystal alignment film coating material for forming a thin film and to a producing method thereof. Also, the present invention relates to an organic thin film formed by use of the thin film forming chemical adsorption material and to a producing method thereof. Further, the present invention relates to a liquid crystal alignment film and to a producing method thereof. Furthermore, the present invention relate to a liquid crystal display using the same and to a producing method thereof and, further particularly, to a liquid crystal alignment film for use in a plane display panel using liquid crystals to display television (TV) picture, computer picture and the like, to a producing method thereof, and to a liquid crystal display device using it.

BACKGROUND ART

In recent years, liquid crystal elements come into wide use rapidly as means for miniaturization of information technology equipment. A liquid crystal alignment film which is the critical component of the liquid crystal elements is subjected to a rubbing process which can be cited as a typical alignment film treatment process. However, the rubbing process has difficulties of deterioration of display quality caused by generation of fine dusts and rubbing lines and others. To avoid these difficulties, rubbingless alignment film treatments, such as an optical alignment film treatment, are now under study.

Known optical alignment film treatments include the process that an alignment film made of polymer, such as polyimide or polyvinyl alcohol, is irradiated with polarized ultraviolet light for alignment film treatment. Another approach was also reported (by Japanese Patent Application No. Hei 8-224,219), in which the optical alignment film treatment is given to the optical alignment film comprising chemical adsorption monomolecular film, as well as to that of polymer such as polyimide. The optical alignment film treatment is performed under the alignment mechanism that admolecules of the film are irradiated with polarized light so as to be re-aligned, so that the liquid crystal molecules are aligned along the polarization direction.

In the case of the alignment film comprising polymer, it has the molecular structure that polymers are complicated densely and irregularly, except its surface part. Because of this, only a part of a surface of the film from which tip portions of the polymer projects out can contribute to the alignment of the liquid crystal molecules. In addition to this, because of uncertainty of the alignment orientation of the side chain, the functional group contributive to the alignment is not always exposed on the surface. Consequently, the part thereof contributive to the alignment of the liquid crystal molecules is obviously smaller in density than that of the monomolecular film, thus suffering the disadvantage that it is difficult to make an adequate control of alignment of the liquid crystals. Also, since the alignment film comprising polymer has large thickness and thus insulative property, it has the problem that transmission of light and electric field to drive the liquid crystal molecules are hindered.

In contrast to this, in the case of the alignment film comprising chemical adsorption monomolecular film, since the functional group contributive to the alignment of the liquid crystal molecules is fully exposed on the surface of the film, adequate control of alignment of the liquid crystals can be obtained. In addition to this, the alignment film of chemical adsorption monomolecular film is in a monomolecular layer form and thus has small thickness, as compared with the alignment film of polymer. Also, since it is chemically adsorbed on the surface of the substrate, it also has excellent adhesion property.

Thus, the conventional alignment film comprising polymer has the problems that adequate control of alignment cannot be obtained and that it has large thickness and thus insulative property. In view of the problems above, there has been developed and provided an alignment film comprising chemical adsorption monomolecular film.

The alignment film comprising chemical adsorption monomolecular film was rather useful for solving the disadvantages mentioned above. However, the admolecules forming the film are merely aligned and arrayed along the polarization direction, so that when the film is heated to high temperature, the alignment stability falls disadvantageously. Consequently, the development is being desired of a useful alignment film of monomolecular film form that is further excellent in thermal stability of alignment.

Incidentally, the conventional liquid crystal display has the structure wherein a pair of substrates, which have transparent electrodes arranged in a matrix form and liquid crystal alignment films formed on the transparent films, are arranged to confront each other, with a given gap therebetween with their liquid crystal alignment films facing inwards, and liquid crystal is sealed in the gap. Now, taking a color liquid crystal display as an example, a typical producing method will be explained below. A polymer membrane is formed on each of a first glass substrate on which pixel electrodes and thin-film transistor (TFT) array are formed and a second glass substrate on which a number of color filters of red, blue and green are formed and common transparent electrodes are further formed thereon. Then, these polymer-coated surfaces of the substrates are subjected to the rubbing to provide alignment characteristic of liquid crystal. Then, the substrates are so arranged that their coated surfaces can face inward and confront each other in the state in which spacers are interposed therebetween and are adhesive bonded around the margins thereof to form an empty cell (a panel structure).

Liquid crystal material, such as twisted nematic liquid crystal, is filled in and tightly sealed in the empty cell, to form the liquid crystal display element. Further, a polarizing plate is arranged on each outside surface of the element and also a backlight is disposed at the outside of the first glass substrate, to thereby produce the liquid crystal display as the optical display element.

In the liquid crystal display thus structured, the TFT of switching elements controls an interelectrode voltage to change the alignment of liquid crystals, so that the transmission of light is switched on and off in a pixel basis to display any desired image. Consequently, the alignment film that controls the alignment of the liquid crystals at the time of no applied voltage bears a significantly important part in exerting an influence directly on the display performance of the device.

Polyimide films have been widely used hitherto as a coating material of the liquid crystal alignment film, in terms of their excellence in affinity to liquid crystal, heat resistance, and adhesion to the substrate. In general, the polyimide film is produced by using either of the following two processes. One is that after liquid solution obtained by polyamic acid of precursor polymer of polyimide being dissolved in organic solvent such as xylene is rotationally applied on to the substrate, that substrate is baked to imidize the polyamic acid, so as to form the polyimide film. Another is that after liquid solution obtained by polyimide itself being dissolved in organic solvent such as DMF (N,N-dimethylformamide), DMAc (dimethylacetamide), butyl cellosolve acetate and N-methyl-2-pyrrolidone is rotationally applied on to the substrate, the solvent is evaporated to form the coating film. The polyimide film thus produced has the following problems, however.

(1) In the process using the polyamic acid of precursor, the baking at high temperature of 250° C. or more is needed for imidization of the polyamic acid. Also, in the process using polyimide itself as well, since there is no proper low-boiling-point solvent for dissolving the polyimide, rather high temperature is required for removal of the solvent. As mentioned above, the organic solvents that may be used for dissolving the polyimide include, for example, DMF, DMAc, butyl cellosolve acetate and N-methyl-2-pyrrolidone. However, these solvents are all high in boiling point (153° C., 165° C., 192° C. and 202° C., respectively) and also are flammable, so that when the film is formed, these solvents must be evaporated and dried at high temperature, while taking explosion-protection into consideration. In the circumstances, a special device for the heating is additionally needed for forming the polyimide film and accordingly the manufacturing costs increase. Also, there is the possibility that e.g. TFT circuits may be damaged by heating.

(2) Since the polyimide is not adequate to form the film, it is hard for the polyimide to produce a coating film of thin and uniform film thickness. Due to this, display unevenness originating from unevenness of the film thickness is generated. Also, since a thick coating film serves as the insulating film, it is hard to realize the liquid crystal display of low voltage drive.

When the polyimide film involving the various problems mentioned above is used as the liquid crystal alignment film and is subjected to the alignment process such as the rubbing process, additional problems are further caused as follows.

① When the coating film has projections and depressions, it cannot be rubbed at its depressed part. The coating film particularly for a larger area panel would not be rubbed uniformly, so that the problems, such as deficiency in alignment, display unevenness and display burn-in, are caused.

② Static electricity is generated on the alignment film, and as such can cause a possible lowering of the TFT function.

③ Further, dust is produced from rubbing material (cotton cloth and the like), and the dust accounts for variations of display unevenness and the gap between the substrates.

These problems become outstanding particularly in the following cases. For example, Japanese Laid-open (unexamined) Patent Publication No. Hei 5-173,135 proposes the method wherein the process that the alignment film is rubbed in a certain direction and further is rubbed in the opposite direction after the concerned part is covered with resist is repeated a given number of times to form a number of areas varied in orientation of alignment of liquid crystal. This method produces the effect in providing a modified viewing angel characteristic to the TN mode of liquid crystal display element having its inherent disadvantage of narrow viewing angle. However, the complicated work that the masking is done for each of divided regions in advance of the rubbing must be repeated, in order to form a number of divided areas varied in orientation of alignment of liquid crystal. This causes the production efficiency of the alignment film to be lowered to a large extent and also causes the dust generation problem into further serious problem.

Under the circumstances, various non-contact alignment modes have been proposed with the aim of solving the problems involved in the rubbing mode.

For example, Japanese Laid-open (unexamined) Patent Publication No. Hei 5-53,118 proposes the technique that a photosensitive composition layer is formed on the substrate and then grooves in specific patterns are formed on the composition layer through the exposure and heating processes, so that the alignment of liquid crystal is provided by the grooves thus formed. However, this technique requires large light energy for forming the grooves. Further, it is difficult for the grooves to be formed uniformly, thus causing the problems of display unevenness and the like. Furthermore, it has the problem that the control of the alignment of the liquid crystal is not sufficient.

Japanese Laid-open (unexamined) Patent Publication No. Hei 7-72,483 proposes the technique that the alignment film forming compound layer including polyimide or precursor of polyimide is directly irradiated with polarized light to polymerize the polyimide and the like, so as to provide the alignment of liquid crystal. However, since this technique uses the polyimide of organic polymer, if the alignment film has large thickness, the problem of increased liquid crystal driving voltage cannot be solved. Further, the technique has an additional problem that anchoring strength of the alignment film to the substrate is insufficient.

Japanese Laid-open (unexamined) Patent Publication No. Hei 7-318,942 proposes the technique that the alignment film having the polymer structure is obliquely irradiated with light to cause additional bond or decomposing reaction of molecular chains of the alignment film to thereby produce the molecular structure having the alignment of liquid crystal. However, this technique is intended for the alignment film comprising organic polymer, such as polyimide, polyvinyl alcohol and polystyrene. Accordingly, this technique cannot dissolve the above-noted problems of the large film thickness, the small anchoring strength of the alignment film for the substrate, and others, either. Also, it is essential for this technique that the alignment film for which a pretilt angle is given is irradiated with light from an oblique direction. However, in order for the alignment film to be accurately irradiated with light from such an oblique direction, a high-precision light irradiation device is required and accordingly the production costs increase to that extent.

Applications of the techniques described by the publications as noted above could form a number of divided areas varied in orientation of alignment of liquid crystal and accordingly could also apply to the TN mode of liquid crystal display element having a narrow viewing angle. However, since the respective techniques have the problems of the large film thickness, the small anchoring strength of the alignment film for the substrate, and others, as mentioned above, the applications thereof could not provide a fully satisfactory liquid crystal alignment film, after all.

One the other hand, a VA (vertical alignment) mode of liquid crystal display capable of realizing high contrast and high-speed response have begun to make a mark in recent years. In this alignment mode, the vertical alignment of liquid crystal molecules can be realized by use of a VA-use liquid crystal alignment film. The VA-use liquid crystal alignment films include the one formed by the polyimide, in which a long-chain alkyl group or a fluoric functional group is introduced into the side chain, being used as the alignment film material. However, such alignment film material is, in general, high in surface energy (e.g. low in water repellency), thus suffering the problem of being inferior in adhesion to the substrate. In addition, since the alignment film is formed of polymer, it is large and uneven in thickness and thus has insulative property, thus suffering the aforementioned problem that transmission of light and electric field to drive the liquid crystal molecules are hindered. Further, although the action of the side chain is the factor contributing to the vertical alignment of the liquid crystal molecules, it is impossible to make the control of allowing the side chain to be efficiently exposed on the boundary between the side chain and the liquid crystal. For this reason, the part of the alignment film to contribute to the alignment of the liquid crystal molecules is apparently low in density, as compared with the monomolecular film, thus suffering the difficulties of adequate control of alignment of liquid crystals.

Meanwhile, in Japanese Laid-open (unexamined) Patent Publication No. Hei 3-7,913 the inventors previously proposed the technique for producing the alignment film having thickness of a level of nanometer with efficiency. This technique uses the monomolecular layer, which is formed by silane-baced chemical adsorption material (which is also called the surface-active agent) being chemically adsorbed on the substrate as the alignment film. This technique can produce the result that a very thin transparent coating film bonded and anchored on the substrate can be formed with ease and efficiency. Besides, it can provide the alignment film having some capability of controlling alignment of liquid crystal molecules without any rubbing process. This technique still has room for improvement on the thermal stability of the alignment and the controllability of the alignment, however.

DISCLOSURE OF THE INVENTION

In consideration of the present situation mentioned above, a group of inventions have been made. It is the primary object of the invention to provide a novel, thin-film forming, chemical adsorption material which is capable of forming a thin-film of a monomolecular layer form and has a photosensitive group which is transparent and stable in a visible light region and causes photochemical reaction in a ultraviolet light region and also provide the producing method thereof.

It is the secondary object of the invention to provide a novel, vertical alignment-use, liquid crystal alignment film having a very small thickness of a level of nanometer that can be uniformly and strongly anchored on the substrate, is excellent in thermal stability and controllability of alignment and wide in viewing angle, capable of high-response and high-contrast control of alignment via the vertical alignment, and can be produced with good productivity and to provide a novel liquid crystal display element using such a liquid crystal alignment film.

Although the group of inventions is based on the same or similar conception, since they are realized by way of different examples, the inventive groups are divided into the first inventive group, the second inventive group and the third inventive group on the basis of their respective relevance. In the following, the contents will be explained in order for each division (each inventive group).

FIRST INVENTIVE GROUP

The inventors of this application have discovered that chemical adsorption material having a chalcone skeleton can be chemical adsorbed on the base substance to form a transparent coating film of a monomolecular layer form and also it has reactivity to light in a far ultraviolet-ultraviolet light (of wavelength of 200 nm to 400 nm) region, while on the other hand, it exhibits stability to light in a visible light (of wavelength of 400 nm to 700 nm) region, and further have made an analysis thereon. As a result of the study, they have completed a novel, thin-film forming, chemical adsorption material (hereinafter it sometimes simply referred to as a chemical adsorption material) and a producing method of this chemical adsorption material.

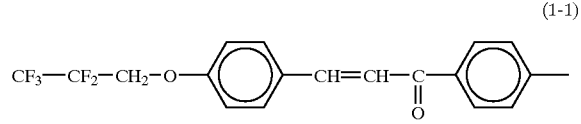

(1-1)

In order to attain the primary object mentioned above, an organic thin film according to the first inventive group comprises at least a functional group expressed by the following chemical formula (1-1) and a —SiX group (X represents halogen) as an end group bonded by siloxane bond:

The functional group expressed by the chemical formula (1-1) includes the chalcone skeleton expressed by the following chemical formula (1-4), so that when the functional group is irradiated with light in the ultraviolet light region, it functions as a photosensitive group and permits the molecules to be cross-linked to each other.

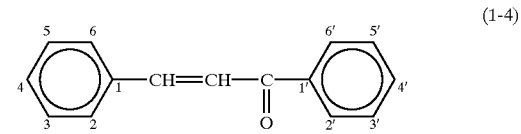

(1-4)

Further, since a perfluoromethyl group (—CF$_3$ group) represented in the chemical formula (1-1) has the minimum critical surface tension of all atoms and groups, so it has the property of repelling the liquid crystals. Also, according to the thin film forming chemical adsorption material having the above-noted constitution, since there is included a SiX group as an end group bonded by the siloxane bond, the Si portion functions as the chemical adsorption group and is allowed to react with a functional group existing on the surface of the base substance to be chemically adsorbed thereon.

The compound expressed by the following chemical formula (1-2) is preferably used as the chemical adsorption material.

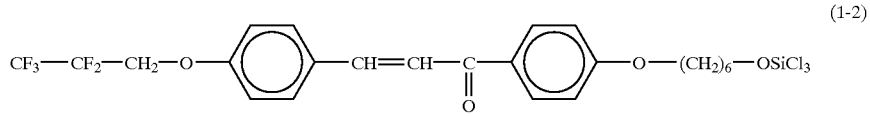

(1-2)

The thin film forming chemical adsorption material having these properties is useful as a functional coating film material for modifying the property of the surface of the base substance, particularly as a liquid crystal alignment film material. For example, when the thin film forming chemical adsorption material is used as the liquid crystal alignment film material, the following operation and effect are provided. The thin film formed by putting the chemical adsorption material into contact with the base substance so as to be chemically adsorbed thereon has the structure of a monomolecular layer form in which molecules are arranged laterally, with their one long axial ends (SiX groups) being bonded to the surface of the base substance and the other ends being oriented to a direction for them to be away from the base substance. This coating film is of very thin of a level of nanometer and is chemically stable and transparent in the visible light region.

On the other hand, since the chemical adsorption material has the properties that a vinyl group portion causes a light reaction by the irradiation of light in the ultraviolet light region, when the chemical adsorption material as was chemically adsorbed on the base substance is irradiated with ultraviolet light, the adsorption molecules is cross-linked to each other. This can provide the liquid crystal alignment film in which the alignment of the adsorption molecules are strically stabilized. Also, when polarized light is used in the irradiation of ultraviolet light, a cross-link reaction can be caused along a specific direction. Accordingly, when the polarizing direction is regulated, the orientation for the adsorption molecules to be aligned can be controlled.

It is to be noted here that with the thin film of a monomolecular layer form having the structure that the chemical adsorption material is adsorbed along the base substance, it is possible for the liquid crystal molecules to enter the spaces (valleys) between the individual adsorption molecules. Consequently, the thin film in which thin film constituent molecules (adsorption molecules) are aligned in a given direction has a specific orientation of liquid crystals. With this thin film, since the constituent molecules of the thin film are each contributive to the orientation of liquid crystals, although the film is a very thin coating film of a monomolecular layer form, it exerts strong control of alignment of liquid crystals. Further, since the end group of the thin film constituent molecule on the front side of the thin film is a perfluoromethyl group having a very small critical surface tension, the liquid crystal molecules can be aligned at a high pretilt angle. Also, since the adsorption molecules are linked and bonded to each other by the cross-link reaction, the alignment properties are prevented from being deteriorated due to external factors such as heat and friction.

In addition, since this coating film is very thin and transparent and also is not an organic polymer film, it hardly serves as an electric resistance film. Consequently, it has significantly advantageous properties as the liquid crystal alignment film that it does not hinder the transmission of light and the electric field to drive the liquid crystals.

In contrast to this, in the conventional liquid crystal alignment film (e.g. a polymer film made of polyimide) in which the long chains are densely and irregularly complicated, only a surface part thereof is contributive to the alignment of the liquid crystals, so that it is hard to obtain adequate controllability of the alignment of the liquid crystals. In the conventional alignment film having the alignment property given by the rubbing, the alignment property is varied or deteriorated by external factors such as heat and friction. Further, since the polymer film made, for example, of polyimide is large in thickness and high in electric resistance, it provides inhibition factors to hinder the transmission of light and the electric field to drive the liquid crystals.

The chemical adsorption material of the present invention can be produced by a producing method comprising at least:

the chemical reaction process 1 that at least 4-(2,2,3,3,3-Pentafluoropropyloxy) benzaldehyde and 4-Hydroxyacetophenone are subjected to aldol condensation reaction to synthesize alcohol having a chalcone skeleton expressed by the following chemical formula (1-3) (chemical reaction process 1); and the chemical reaction process 2 that after the chemical reaction process 1, $SiX_4$ (X represents halogen) is subjected to dehydrohalogenation reaction with alcohol having the chalcone skeleton under an inert gas atmosphere, to synthesize chemical adsorption material having a characteristic group expressed by the following chemical formula (1-1) and a —O—$SiX_3$ group:

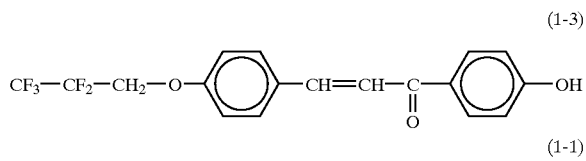

This can produce the chemical adsorption material that can permit the molecules to be cross-linked with each other and also allow them to react with the surface functional group existing on the surface of the base substance so as to be chemically adsorbed thereon when irradiated with the light in the ultraviolet light region.

Further, the chemical adsorption material include a compound expressed by the following chemical formula (1-2):

[Second Inventive Group]

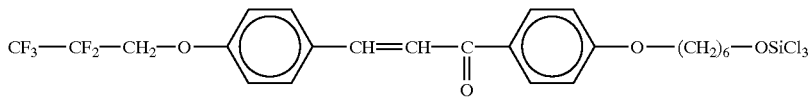

In order to attain the secondary object mentioned above, an organic thin film according to the secondary inventive group comprises an aggregation of adsorption molecules directly bonded and anchored to or indirectly bonded and anchored to a surface of a base substance through another material layer, wherein the adsorption molecules have a characteristic group expressed by the following chemical formula (1-2) and a —O—Si bond group at a molecular end group:

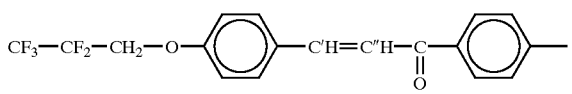

The organic thin film having the constituent mentioned above comprises the aggregation of adsorption molecules arrayed along the surface of the base substance in the state in which they are chemically adsorbed on the base substance at one end thereof (on the —O—Si bond group side) and are projected out from the surface of the base substrate in a direction of being away therefrom. In the aggregation of adsorption molecules comprising the characteristic group expressed by the chemical formula (2-1) and the —O—Si bond group, since the individual adsorption molecules are strongly bonded and anchored to the substrate via the chemical bonding, the peeling of the coating film is prevented. Consequently, it has an excellent anti-peeling property.

When this organic thin film is applied to the liquid crystal alignment film, the liquid crystal molecules can enter the spaces (valleys) between the adsorption molecules in the aggregation of adsorption molecules and are then controlled to the tilt and/or orientation of alignment of the liquid crystals with respect to the substrate (hereinafter it is collectively called the alignment direction). Consequently, although the film is a very thin coating film of a monomolecular layer form, it exerts strong control of alignment of liquid crystals. Further, since it has a perfluoromethyl group (—$CF_3$ group) having a very small critical surface tension as the end group of the thin film constituent molecule on the front side of the thin film, the liquid crystal molecules can be aligned at a high pretilt angle. Also, since the liquid crystals can strongly be bonded to the substrate through Si atoms and also the adsorption molecules can strongly be bonded to each other through Si, the liquid crystal alignment film of excellent durability can be obtained.

The base substances that may be used include, for example, a substrate made of glass and the like and those made of metal, ceramics, glass, plastics, polymer, paper, fiber and leather. Further, electrodes (including wires) and/or other material layers may be formed on the substrate.

The adsorption molecules forming the organic thin film may be molecules in which the chalcone skeleton of the functional group shown in the chemical formula (2-1) and —O—SiX group are directly bonded to each other or the functional groups cited below as an example are indirectly bonded to the chalcone skeleton via the —O— bond.

(1) Hydrocarbon radicals such as —$(CH_2)n$ (where n is an integer number of 1–20) and —$C_6H_5$;

(2) Hydrocarbon radicals of the carbon-carbon double bond or the carbon-carbon triple bond being included in a part of the hydrocarbon radicals as listed in the above item (1) (except —$CH_2$);

(3) Functional groups of which hydrogen of hydrocarbon radicals of the items (1) and (2) above is replaced with other functional group (e.g. a methyl group, a halogenated methyl group, a hydroxyl group, a cyano group, etc.) and/or atoms (e.g. F, Cl, Br, I, etc.); and (4) Functional groups in which the C—C bond of hydrocarbon radicals of the above items (1) and (2) is partly replaced with the C—O—C (ether) bond or the C—CO—C—(carbonyl) bond.

The absorption molecules explained above include those having the chemical constituent expressed, for example, by the following chemical formula (2-2):

of their major exes with respect to the surface of the substrate and/or in orientation of alignment thereof. The divided regions means the regions formed by dividing a single picture element into a number of regions in a pattern-like form. When the film is formed as the so-called, multi-domain type liquid crystal alignment film in which the alignment direction of the adsorption molecules are controlled in each of the minute regions into which the one picture element is divided in a pattern, the light transmitting in each picture element is formed by a number of bundles of rays different in angle from each other. Thus, the dependency of the display on the viewing angle is reduced.

In the constituent above, the adsorption molecules of the aggregation of adsorption molecules may be cross-linked to each other via a boning line(s) of C' and/or C" in the chemical formula (2-1) or (2-2). Since the adsorption molecules are strongly anchored to each other via the cross-link bond, the tilt and the alignment direction of the adsorption molecules are prevented from being varied by external factors such as friction and heat. Consequently, the organic thin film having high reliability can be obtained.

In the constituent above, the organic thin film may have film thickness of 0.5 nm or more to less than 10 nm. With the film thickness of this range, the efficiency of alignment is high in the relation with the film thickness and also the transmission of light and the electric field are not unnecessarily hindered. Consequently, when the organic film is applied to the liquid crystal alignment film, the usability is further improved.

In the constituent above, the organic thin film may be formed by a thin film of a monomolecular layer form. The thin film of a monomolecular layer form can provide the result that when applied to the liquid crystal alignment film, the individual adsorption molecules are directly contributive to the alignment of the liquid crystal molecules. Thus, the liquid crystal alignment efficiency is considerably improved in the relation with the film thickness.

In the constituent above, the organic thin film may comprise an aggregation of adsorption molecules of various kinds. The organic thin film comprising the aggregation of adsorption molecules of various kinds can produce the organic thin film having multifunction.

When the organic thin firm is applied to the liquid crystal alignment film, that liquid crystal alignment film can become an alignment film that develops a desired pretilt angle for the liquid crystal molecules.

In the constituent above, the liquid crystal alignment film may comprises the aggregation of adsorption molecules of various kinds, and the liquid crystal molecules may be aligned at a desired pretilt angle by changing a constituent ratio between the various kinds of adsorption molecules.

It is to be noted here that in addition to the adsorption molecules having a characteristic group expressed by the chemical formula (2-1) and a —O—Si bond group at a molecular end group, the adsorption molecules that may be

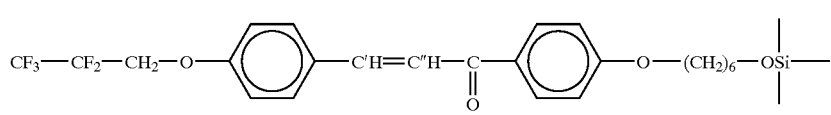

(2-2)

The aggregation of adsorption molecules is permitted to be aligned in a given direction. When the organic thin film is used as the liquid crystal alignment film, this can provide a uniform liquid crystal alignment property to the liquid crystal alignment film.

In this constituent, the adsorption molecules in adjoining divided regions may be differentiated from each other in tilt used include, for example, adsorption molecule having a —O—Si group and a long chain alkyl group (number of carbon: 7 or more to 18 or less) and adsorption molecule having a —O—Si bond group and a long chain fluorocarbon group (number of carbon: 7 or more to 18 or less). In addition, the adsorption molecule in which a cyano group, an ester group, a chloro group or a bromo group is bonded to an end of the alkyl group and fluorocarbon group can also be cited. Further, these adsorption molecules may be adsorption molecules having a characteristic group expressed by the chemical formula (2-1).

Next, the producing method of the organic thin film of the present invention will be described. The inventive producing method of an organic thin film comprising an aggregation of adsorption molecules directly bonded and anchored to or indirectly bonded and anchored to a surface of a base substance through another material layer via chemical adsorption, the producing method comprising: the process that chemical adsorption material having a characteristic group expressed by the following chemical formula (2-1) and a —O—Si bond group at a molecular end portion thereof is at least dissolved in non-water-borne solvent, to prepare chemical adsorption solution: the process that the chemical adsorption solution is put into contact with the surface of the base substance, so that the chemical adsorption material in the chemical adsorption solution is chemically adsorbed on the surface of the base substrate; and the solution draining and drying process that the surface of the base substance to which the chemical adsorption material was bonded is cleaned by use of the non-water-borne solvent and, thereafter, the base substance is stood up in a specific direction to cut and dry the cleaning solution:

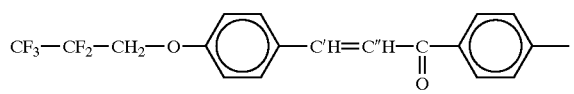

(2-1)

The producing method above may further comprises the polarized ultraviolet irradiation process that after the solution draining and drying process, the adsorption molecules on the surface of the base substance are irradiated with polarized ultraviolet light, so that they are cross-linked to each other via a bonding line of a carbon-carbon double bond portion of the chemical formula (2-1).

The producing method above may be so constituted that a series of alignment film treatment processes comprising the solution draining and the drying process and a polarized ultraviolet irradiation process are repeated a number of times in such a manner that the solution draining and drying process returns back again from the polarized ultraviolet irradiation process, and each time when repeated, the solution draining and drying direction is varied and that the polarized ultraviolet light irradiation region and polarized ultraviolet light irradiation direction, or the polarized ultraviolet light irradiation region and polarized ultraviolet light irradiation angle, or the polarized ultraviolet light irradiation region, polarized ultraviolet light irradiation direction and polarized ultraviolet light irradiation angle, are varied, whereby the adsorption molecules are varied in tilt of their major exes with respect to the surface of the base substance and/or in orientation of alignment thereof from one divided region to another of a number of divided regions into which a region corresponding to one picture element is divided in a pattern-like form. This constitution enables the organic thin film suitable for the multi-domain alignment to be produced reliably and with improved productivity.

In the producing method, aprotic solvent may be used as the non-water-borne solvent for use in cleaning so that the unreacted chemical adsorption material can be cleaned and removed from the surface of the base substance by use of the aprotic solvent, to produce a thin film of a monomolecular layer form.

Alternatively, a mixed solvent of aprotic solvent and protic solvent may be used as the non-water-borne solvent for use in cleaning, so that unreacted chemical adsorption material can be cleaned and removed from the surface of the base substance by use of the mixed solvent, to produce a thin film of a monomolecular layer form. The use of the mixed solvent is of desirable in that the chemical adsorption material dissolving capability and evaporation speed can be adequately adjusted.

The significance of the constitutions above will be described. When the solution of the chemical adsorption material having the characteristic group expressed by the chemical formula (2-1) and the —O—Si bond group at a molecular end portion thereof is put into contact with the substrate, the chemical adsorption material is allowed by react with the surface functional group having active hydrogen on the surface of the substrate to be chemically adsorbed thereon, so as to form an organic thin film. The organic thin film comprises the aggregation of adsorption molecules whose one long axial ends (—O—Si bond group) are bonded to the surface of the base substance and whose other ends are oriented to a direction for them to be away from the base substance. When this organic thin film comprising the aggregation of adsorption molecules is applied to the liquid crystal alignment film, the liquid crystal molecules can enter the spaces (valleys) between the adsorption molecules and are then controlled to the alignment direction of the liquid crystal molecules with respect to the substrate. Consequently, the alignment direction of the liquid crystal molecules can be controlled by regulating the alignment direction of the adsorption molecules.

On the other hand, the compound having the characteristic group expressed by the chemical formula (2-1) has the properties that it is transparent and chemically stable in the visible light region and also high in sensitivity to ultraviolet light at the carbon-carbon double bond portion thereof. Consequently, when the adsorption molecules are chemically adsorbed on the substrate and then are irradiated with ultraviolet light, they can be cross-linked to each other through the carbon-carbon double bonding. In this process, when the polarized ultraviolet light is used, the cross-link direction can be controlled to a specific direction corresponding to the polarizing direction of the polarized light. Then, the adsorption molecules on the surface of the substrate are re-aligned by the irradiation of the polarized light and the re-alignment is provided by the molecules being cross-linked to each other, and as such can produce the resistance to the external factors such as heat and friction.

The chemical adsorption material having the characteristic group expressed by the chemical formula (2-1) and the —O—Si bond group at a molecular end portion thereof that may be used include a compound expressed by the following chemical formula (2-2).

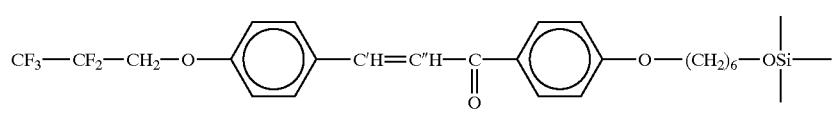

(2-2)

The chemical adsorption material expressed by the chemical formula (2-2) can be chemically adsorbed on the surface of the base substance with ease. Also, the material is strong in bond and high in light-sensitivity at the carbon-carbon double bond portion thereof. In addition, since this material has a perfluoromethyl group at the end group thereof on the front side of the film, it can permit the liquid crystal molecules to be aligned at a high pretilt angle. From the foregoing, the producing method using the compound of chemical formula (2-2) can produce the organic thin film suitably used as the liquid crystal alignment film with improved productivity.

The principal part of the producing method will further be explained. In the solution draining and drying process according to the producing method of the present invention, non-adsorbed chemical adsorption material existing in surplus on the surface of the substrate is first removed by the cleaning process and then the non-water-borne cleaning solvent is dried and removed in the solution draining and drying process. Through this series of operations, the thin film of a monomolecular layer form in which the adsorption molecules are aligned in the solution draining and drying direction can be formed on the substrate. However, this alignment of the adsorption molecules provided by a solution draining and drying process is varied by another solution draining and drying process and is subjected to change by external factors (e.g. heat and friction). Accordingly, this alignment is referred to as "the tentative alignment" in this specification.

Further, in the polarized ultraviolet light irradiation process, the surface of the thin film subjected to the tentative alignment (the aggregation of adsorption molecules) is irradiated with polarized ultraviolet light. The adsorption molecules having the characteristic group expressed by the chemical formula (2-1) have high light-sensitivity. Consequently, the adsorption molecules are allowed to react with each other at the carbon-carbon double bonding portion by the irradiation of polarized ultraviolet light and are cross-linked in a specific direction corresponding to the polarizing direction through the bonding line of the carbon. It is to be noted that the polarizing direction may be identical with the tentative alignment direction or different from it. In either case, the adsorption molecules can be re-aligned in a specific direction corresponding to the polarizing direction by the irradiation of polarized light. However, the solution draining direction and the polarizing direction should not be crossed exactly at 90 degree, but should be somewhat, or preferably some degrees or more, out of position therefrom. This is because, if they are crossed exactly at 90 degree, there is the possibility that the individual molecules could be oriented in two random directions.

The reason therefor has not yet fully clarified, but it was experimentally confirmed that when the thin film, after tentatively aligned, was irradiated with polarized ultraviolet light, the cross link proceeded in a specific direction smoothly to provide an improved alignment treatment effect by the polarized ultraviolet light.

In this specification, in order to differ from the tentative alignment, the alignment performed via the irradiation of the polarized ultraviolet light is called "the re-alignment". Further, the molecules as were chemically adsorbed on the substrate are called "chemical adsorption material". Further, it was experimentally confirmed that the thin film formed by the adsorption molecules being chemically adsorbed on the substrate had thickness of a level generally equal to molecular length of the adsorption molecules (a level of nanometer).

In this connection, the difference between the organic thin film as the liquid crystal alignment film according to the present invention and the conventional liquid crystal alignment film is as follows. In the conventional liquid crystal alignment film (e.g. a polymer film made of polyimide) in which the long chains are densely and irregularly complicated, only a surface part thereof is contributive to the alignment of the liquid crystals, so that it is hard to obtain adequate controllability of the alignment of the liquid crystals. In addition, in the conventional alignment film having the alignment property given by the rubbing, the alignment property is varied or deteriorated by external factors such as heat and friction. Further, since the polymer film made, for example, of polyimide is large in thickness and high in electric resistance, it provides inhibition factors to hinder the transmission of light and the electric field to drive the liquid crystals.

On the other hand, even the liquid crystal alignment film comprising the thin film of a monomolecular layer form is insufficient in alignment stability, if it is the alignment film wherein the adsorption molecules are not cross-linked to each other. For example, the chemical adsorption material described in the above-mentioned Japanese Laid-open (unexamined Patent Publication No. Hei 3-7,913 has no photosensitive group, as such cannot allow the adsorption molecules to be chemically bonded to each other. The liquid crystal alignment film made by using this material has the disadvantage that when it is heated around 200° C., the alignment property deteriorates easily.

Next, description will be given on the liquid crystal display of the present invention using the above-mentioned organic thin film as the liquid crystal alignment film. The liquid crystal display of the present invention comprising a pair of opposed substrates; a liquid crystal alignment film formed at least on a surface of a substrate having electrodes of the pair of substrates; and liquid crystals accommodated in a cell gap between the pair of opposed substrates, wherein the liquid crystal alignment film comprises an aggregation of adsorption molecules bonded and anchored directly on a surface of the substrate forming the electrodes thereon or indirectly bonded and anchored thereon through another material layer via chemical adsorption, and wherein the aggregation of adsorption molecules include adsorption molecule having a characteristic group expressed by the following chemical formula (2-1) and a —O—Si bond group at a molecular end group:

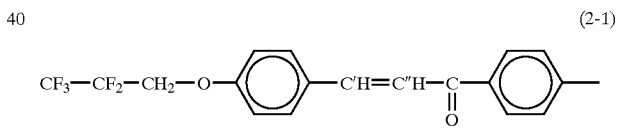

(2-1)

In the above constitution, a pretilt angle and/or a pretilt orientation of the adsorption molecules accommodated in the cell gap are controlled by tilt and/or orientation of alignment of the adsorption molecules' major axes with respect to surface of the substrate.

In the liquid crystal display thus constructed, the adsorption molecules may be differentiated from each other in tilt and/or orientation of alignment of their major axes with respect to the surface of the substrate from one divided region to another of adjoining divided regions into which a single picture element is divided in a pattern-like form.

An in-plane switching type liquid crystal display of the present invention comprises pixel electrodes and opposed electrodes, which are arranged on a substrate, and a liquid crystal alignment film formed on a surface of the substrate on which the electrode are arranged, wherein the liquid crystal alignment film comprises an aggregation of adsorption molecules bonded and anchored directly on a surface of the substrate forming the electrodes thereon or indirectly bonded and anchored thereon through another material layer via chemical adsorption, and wherein the aggregation of adsorption molecules include adsorption molecule having a characteristic group expressed by the following chemical formula (2-1) and a —O—Si bond group at a molecule end group:

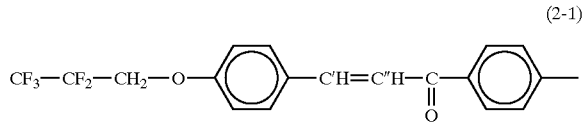

(2-1)

In the liquid crystal display (including the in-plane switching type one, same applies to the following), a pretilt angle and/or a pretilt orientation of the adsorption molecules accommodated in the cell gap are be controlled by tilt and/or orientation of alignment of the adsorption molecules' major axes with respect to the surface of the substrate.

The adsorption molecules forming the liquid crystal alignment film may be cross-linked to each other via a boning line(s) of C' and/or C" in the chemical formula (2-1) or (2-2).

The adsorption molecule having the characteristic group expressed by the chemical formula (2-1) and the —O—Si bond group may have the structure shown in the following chemical formula (2-2).

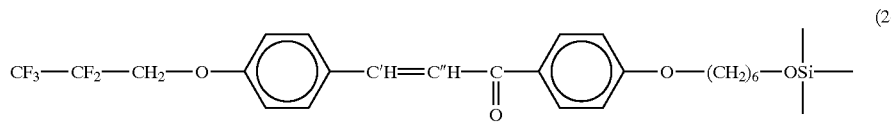

(2-2)

The liquid crystal alignment film preferably has film thickness of 0.5 nm or more to less than 10 nm.

The liquid crystal alignment film may preferably be a thin film of a monomolecular layer form. The liquid crystal alignment film of a monomolecular layer form can provide a considerably reduced degree of hindrance of the electric field to drive the liquid crystals and also can prevent hindering the transmission of light even when it is arranged in a light transmission path. Consequently, the liquid crystal display that can be driven at low voltage and is excellent in brightness can be realized.

Incidentally, an ideal monomolecular layer means a layer in which individual constituent molecules are arranged along the surface of the substrate without overlapping with each other, but realistically it is not easy to form such a complete monomolecular layer. Even when the monomolecular layer is not complete, the object of the present invention can be fully achieved. Accordingly, the termination of "thin film of a monomolecular layer form" used in the specification is intended to cover any thin film of a level of thin film that can be considered as a generally monomolecular layer. For example, the thin film of a monomolecular layer form of the present invention covers a thin film having at a part thereof a multi-molecular layer formed by non-adsorbed molecules being laid on the adsorption molecules adsorbed on the substrate; and a layer formed by a number of molecules that are continuously bonded in such a form that the molecules that are not directly bonded and anchored to the substrate by themselves are bonded to the molecules directly bonded thereto and further other molecules are bonded to the molecules that are not directly bonded thereto.

While the description above is given on the condition that an aggregation of adsorption molecules are composed of only one chemical adsorption material, other adsorption material may be mixed in the adsorption molecules according to the present invention.

Next, the producing methods of the liquid crystal display of the present invention will be described. The present invention provides a producing method of a liquid crystal display having a liquid crystal alignment film comprising an aggregation of adsorption molecules directly bonded and anchored to or indirectly bonded and anchored to a surface of a substrate forming thereon electrodes through another material layer via chemical adsorption, the producing method comprising: the process that chemical adsorption material having a characteristic group expressed by the following chemical formula (2-1) and a —O—Si bond group at a molecular end portion thereof is dissolved in non-water-borne solvent, to prepare chemical adsorption solution: the process that the chemical adsorption solution is put into contact with the surface of the substrate forming the electrodes thereon, so that the chemical adsorption material in the chemical adsorption solution is chemically adsorbed on the surface of the substrate; and the solution draining and drying process that the surface of the substrate to which the chemical adsorption was bonded is cleaned by use of the non-water-borne cleaning solvent and, thereafter, the substrate is stood up in a specific direction to cut and dry the cleaning solution:

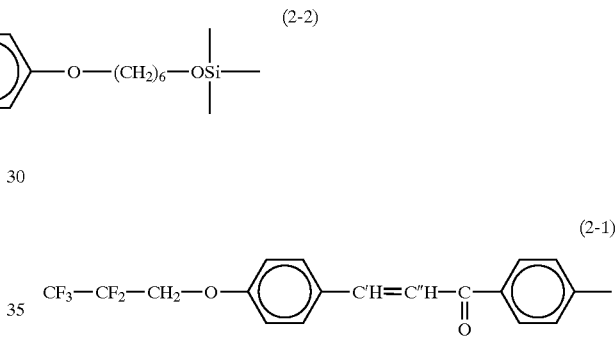

(2-1)

The producing method above may further comprises the polarized ultraviolet irradiation process that after the solution draining and drying process, the adsorption molecules on the surface of the substrate are irradiated with polarized ultraviolet light, so that they are cross-lined to each other via a bonding line of a carbon—carbon double bond portion of the chemical formula (2-1).

In the producing method above, a series of alignment film treatment processes comprising the solution draining and the drying process and the polarized ultraviolet irradiation process are repeated a number of times in such a manner that the solution draining and drying process returns back again from the polarized ultraviolet irradiation process; and each time when repeated, the solution draining and drying direction is varied and that the polarized ultraviolet light irradiation region and polarized ultraviolet light irradiation direction, or the polarized ultraviolet light irradiation region and polarized ultraviolet light irradiation angle, or the polarized ultraviolet light irradiation region, polarized ultraviolet light irradiation direction and polarized ultraviolet light irradiation angle, are varied, whereby the adsorption molecules are varied in tilt of their major exes with respect to the surface of the substrate and/or in orientation of alignment thereof from one divided region to another of a number of divided regions into which a region corresponding to one picture element is divided in a pattern-like form. This method can reliably and efficiently produce the liquid crystal display having the multi-domain type liquid crystal alignment film which is varied in alignment direction from one divided region to another of the divided regions divided in a pattern-like form.

Aprotic solvent may be used as the non-water-borne solvent for use in cleaning, so that unreached chemical adsorption material is cleaned and removed from the surface of the substrate by use of the aprotic solvent, to produce a thin film of a monomolecular layer form.

Also, a mixed solvent of aprotic solvent and protic solvent may be used as the non-water-borne solvent for use in cleaning, so that unreacted chemical adsorption material is cleaned and removed from the surface of the substrate by use of the mixed solvent, to produce a thin film of a monomolecular layer form.

The chemical adsorption material having a characteristic group expressed by the chemical formula (2-1) and a —O—Si bond group at a molecular end portion thereof may be a compound expressed by the following chemical formula (2-2).

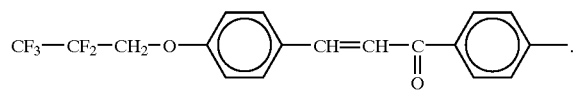

(1-1)

The —SiX group of the end group causes a reaction with a surface functional group having active hydrogen existing on a surface of a base substance, to release HX therefrom, so that it can serve as adsorbate to chemically adsorb the material on the surface of the base substance of adsorbent. This enables a thin film to be formed in the monomolecular layer form in which molecules are arranged laterally, with

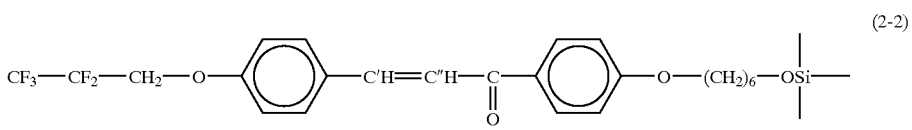

(2-2)

These and other objects, features and advantages of the present invention will fully be understood by reference to the following description. Also, the merits of the present invention will become more apparent upon reading the following description referring to the accompanying drawings.

BEST MODE FOR CARRYING OUT THE INVENTION

FIRST INVENTIVE GROUP

Figure 1:
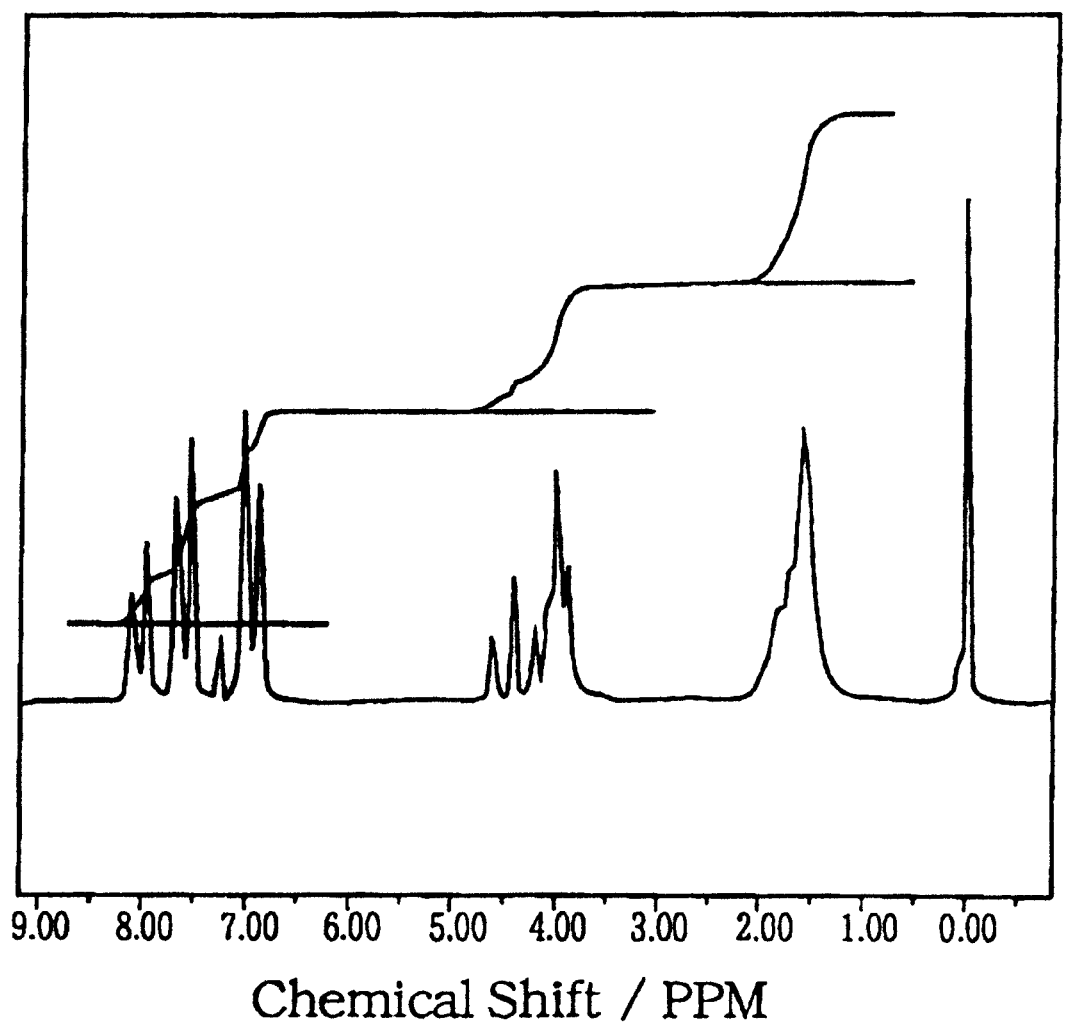
FIG. 1 is a $^1$H-NMR spectrum chart of a final product synthesized in Example 1 according to the first inventive group.

In the following, description is given on an embodiment according to the first inventive group.

A thin-film forming chemical adsorption material of the present invention has been completed, considering that the chalcone skeleton is high in light-sensitivity. The thin-film forming chemical adsorption material of the invention comprises at least a functional group expressed by the following chemical formula (1-1) and a —SiX group (X represents halogen) as an end group bonded by siloxane bond.

their one long axial ends (SiX groups) being bonded to the surface of the base substance and the other ends being oriented to a direction for them to be away from the base substance. Specifically, the surface functional groups to be allowed to react with the —SiX group include the groups having affinity, such as a —OH group, a —COOH group, a —NH$_2$ group, a —NH group and a —SH group.

In addition, since the thin-film forming chemical adsorption material of the invention has the chalcone skeleton, when it is irradiated with light in the region of far ultraviolet·ultraviolet light (200–400 nm), the admolecules can be cross-linked to each other by the photo-polymerization reaction. On the other hand, since the thin-film forming chemical adsorption material of the invention exhibits chemical stability and transparent and colorless for the light in the visible light region (400–700 nm), it is a suitable compound as the liquid crystal alignment film material.

Further, since a perfluoromethyl group exists in the end group in the film on its front side, the critical surface tension is so small that the liquid crystal alignment film having the property of repelling the liquid crystal molecules can be formed.

It should be noted that the chalcone skeleton and —O—SiX group may be directly bonded to each other or the functional groups cited below as an example may be indirectly bonded to the chalcone skeleton via the —O-bond.

(1) Hydrocarbon radicals such as —(CH$_2$) n (where n is an integer number of 1–20) and —C$_6$H$_5$;

(2) Hydrocarbon radicals of the carbon—carbon double bond or the carbon—carbon triple bond being included in a part of the hydrocarbon radicals as listed in the above item (1) (except —CH$_2$);

(3) Functional groups of which hydrogen of hydrocarbon radicals of the items (1) and (2) above is replaced with other functional group (e.g. a methyl group, a halogenated methyl group, a hydroxyl group, a cyano group, etc.) and/or atoms (e.g. F, Cl, Br, I, etc.); and (4) Functional groups in which the C—C bond of hydrocarbon radicals of the above items (1) and (2) is partly replaced with the C—O—C (ether) bond or the C—CO—C-(carbonyl) bond.

Examples of the chemical adsorption material expanded above include, for example, the compound expressed by the chemical formula (1-2) given below.

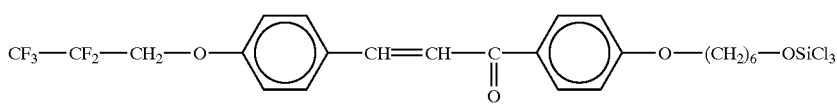

The thin-film of the monomolecular layer form comprising the chemical adsorption material of the present invention as described above produces the structure described below.

The thin-film forming chemical adsorption material of the invention is allowed to have the structure of the admolecules being cross-linked to each other via the carbon—carbon double bond in the chalcone skeleton when irradiated with light in the region of far ultraviolet·ultraviolet light (200–400 nm). Thus, it can have the structure in which the alignment of the thin-film constituent molecules is sterically stabilized. When this thin film is used as the liquid crystal alignment film, that alignment film will become excellent in heat resistance and abrasion proof. Furthermore, since the sterical stabilization serves to increase the control of alignment of liquid crystals, the thin-film forming chemical adsorption material of the invention has the excellent alignment capability. In addition, since the perfluoromethyl group (—$CF_3$ group) of very small critical surface tension exists in the end group in the thin-film constituent molecule on its front side, the liquid crystal alignment film has the property of repelling the liquid crystals, and as such can allow the liquid crystal molecules to be aligned at a high pretilt angle. Also, the thin-film forming chemical adsorption material of the invention enables the cross-link reaction to be caused along the direction parallel to the polarized direction by the irradiation with ultraviolet light polarized in a specified direction and thereby it can have the structure wherein the alignment orientation of the admolecules is controlled. As a result of this, the orientation for the liquid crystal molecules to be aligned can be controlled, such as, for example, the liquid crystal molecules being aligned in the specified direction. Further, since the chalcone derivative has transparency for the visible light in the region of wavelength of not less than 400 nm, it shows very high transmission property and thereby the thin film having excellent transparency can be formed. Furthermore, this coating film has significantly small thickness of a level of nanometer.

In the following, description will be given on the producing method of the thin-film forming chemical adsorption material.

First, 4-(2,2,3,3,3-pentafluoropropyloxy) benzaldehyde and 4-hydroxyacetophenone are subjected to aldol condensation reaction to synthesize the alcohol having the chalcone skeleton expressed by the following chemical formula (1-3) (chemical reaction process 1). Then, SiX4 is subjected to dehydrohalogenation reaction with the alcohol having the chalcone skeleton under an inert gas atmosphere, to synthesize the chemical adsorption material having the characteristic group expressed by the following chemical formula (1-1) and the —O—$Six_3$ group (Chemical reaction process 2). An additional reaction process may further be performed of adding the other functional group, such as hydrocarbon radical, via the —O— bond at the 4' position of the chalcone skeleton. This additional reaction process must then be performed after the chemical reaction process 1. By the processes mentioned above, the chemical adsorption material according to the present invention can be produced with efficiency.

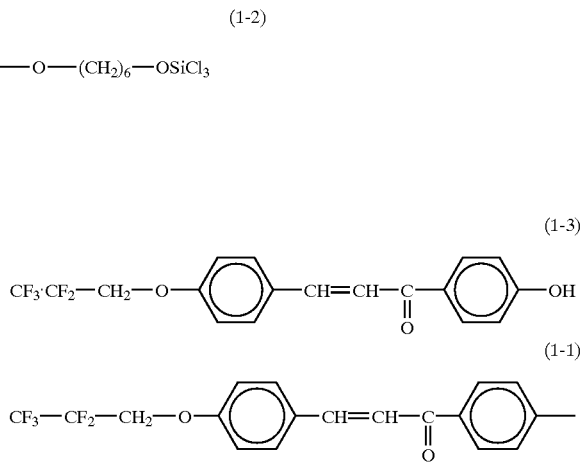

It should be noted that the above-mentioned producing method is not exclusive for the chemical adsorption material of the present invention. For example, the chemical adsorption material of the present invention may be synthesized by the reaction of adding the characteristic group to the chalcone derivative used as starting material.

EXAMPLE 1-1

The process for synthesizing the novel chemical adsorption material according to the present invention will be described in order by dividing the process into the reaction processes 1–4. The chemical adsorption material synthesized below (silane-based chemical adsorption material) is the compound expressed by the chemical formula 1-2 given above.

Reaction process 1:

1,675 ml of Sodium hydride (60%) and HMPA (hexamethylphosphoramide) was charged with a reaction flask (internal volume: 5L) and was cooled by freezing. Then, 380 g (2.53 mol) of 1H,1H-pentafluoropropanol was dropped into it at 15° C. for 3 hours. Thereafter, the reaction flask was restored to room temperature and the charged compound was agitated for 1 hour under the room temperature.

Then, after the mixture was cooled down to 10° C. or less, 209.4 g (1.69 mol) of p-fluorobenzaldehyde was dropped into the mixture for 1 hour. Thereafter, it was agitated at the same temperature for 3 hours.

The reactant thus obtained was poured into 3.4L of a 5% hydrochloric acid to extract the reaction product by using ethyl acetate and rinse it by using dilute hydrochloric acid. Then, the reaction product was dried by using magnesium sulfate anhydride and thereafter the solvent was distilled off to obtain crude crystals. The crude crystals thus obtained were purified by use of silica gel column (Moving phase: n-hexane/ethyl acetate=10/1) to obtain 330.0 g of 4-(2,2,3,3,3-pentafluoropropyloxy) benzaldehyde (GLC purity: 95%, Yield: 76.9%).

The chemical reaction formula (1–5) in this process is given below.

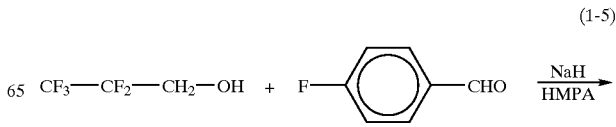

-continued

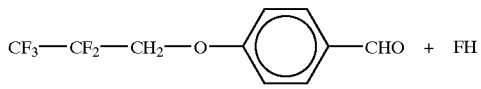

Reaction process 2:

330 g (1.30 mol) of 4-(2,2,3,3,3-pentafluoropropyloxy) benzaldehyde, 176.7 g (1.30 mol) of 4-hydroxyacetophenone, 33.0 g of piperidine, 33 ml of acetic acid, 3.3L of toluene were charged with the reaction flask (internal volume: 5L) and agitated at 110° C. for 5 days.

After the reaction flask was cooled down to room temperature, the reaction solution was poured into 2.1L of 1N hydrochloric acid and the deposited crystals were taken out by filtration.

Then, after the crystals were washed by water, they were dissolved in 15L of chloroform. Then, they were dried by using magnesium sulfate anhydride and, thereafter, the solvent was distilled off, to obtain 322.0 g of 4-(2,2,3,3,3-pentafluoropropyloxy)-4'-hydroxychalcone (GLC purity: 98%, Yield: 66.6%).

The chemical reaction formula (1–6) in this process is given below.

(1-6)

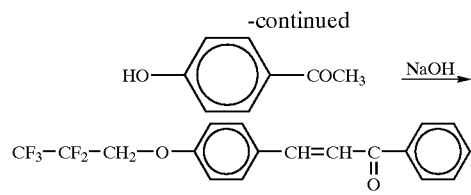

Reaction process 3:

322 g (0.866 mol) of 4-(2,2,3,3,3-pentafluoropropyloxy)-4'-hydroxychalcone and 3L of dry DMF (N,N-dimethylformamide) were charged with the reaction flask (internal volume: 5L) in a stream of argon and 34.6 g (0.865 mol) of sodium hydride (60% was added thereto under freezing for 30 minutes. Thereafter, the reaction flask was heated up to room temperature, the reactant was agitated for 20 hours.

Then, 117.7 g (0.865 mol of 6-chlorohexanol was dropped into the mixture at the same temperature for 20 minutes and, thereafter, the reactant was heated to 80° C. to be allowed to react for 23 hours. Then, reaction solution was poured into ice water to extract the reaction product by using ethyl acetate. The solution was washed by water and then magnesium sulfate was added into the ethyl acetate extracted solution for treatment of it. Thereafter, the solvent was distilled off to obtain crude crystals.

The crude crystals thus obtained were purified by use of silic gel column (Moving phase: n-hexane/ethyl acetate=2/1). Further, they were recrystallized by purifying them in silica gel column (Moving phase: n-hexane/ethyl acetate=1/1) to obtain 123.0 g of 4-(2,2,3,3,3-pentafluoropropyloxy)-4'-(6'-hydroxyhexyloxy) chalcone (HPLC purity: 98%, Yield: 30.1%).

The chemical reaction formula (1–7) in this process is given below.

(1-7)

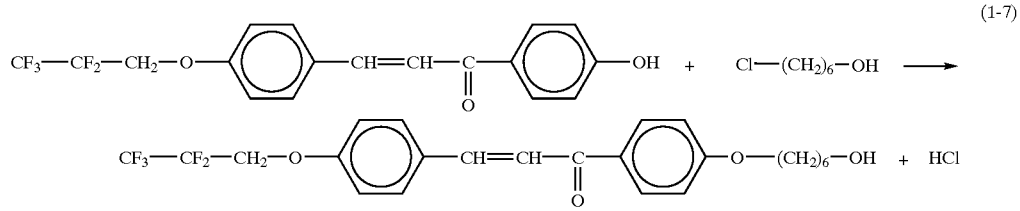

Reaction process 4:

60.0 g (0.127 mol) of 4-(2,2,3,3,3-pentafluoropropyloxy)-4'-(6'-hydroxyhexyloxy) chalcone and 240.0 g (1.41 mol) of silicon tetrachloride were charged with flask (internal volume: 500 ml) in a stream of argon and agitated for 1 hour at room temperature.

Surplus silicon tetrachloride was distilled off to obtain 69.4 g of 4-(2,2,3,3,3-pentafluoropropyloxy)-4'-(6'-trichlorosilyloxyhexyloxy) chalcone (Yield: 90.2%).

The chemical reaction formula (1–8) in this process is given below.

(1-8)

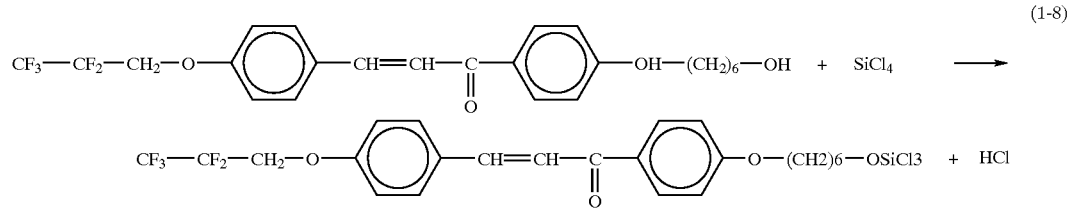

The final product thus obtained was analyzed by measuring $^1$H-NMR spectrum. The $^1$H-NMR spectrum is shown in FIG. 1. The peaks in FIG. 1 support that the final product has the chemical structure expressed by the chemical formula (1-1) above.

Figure 2:
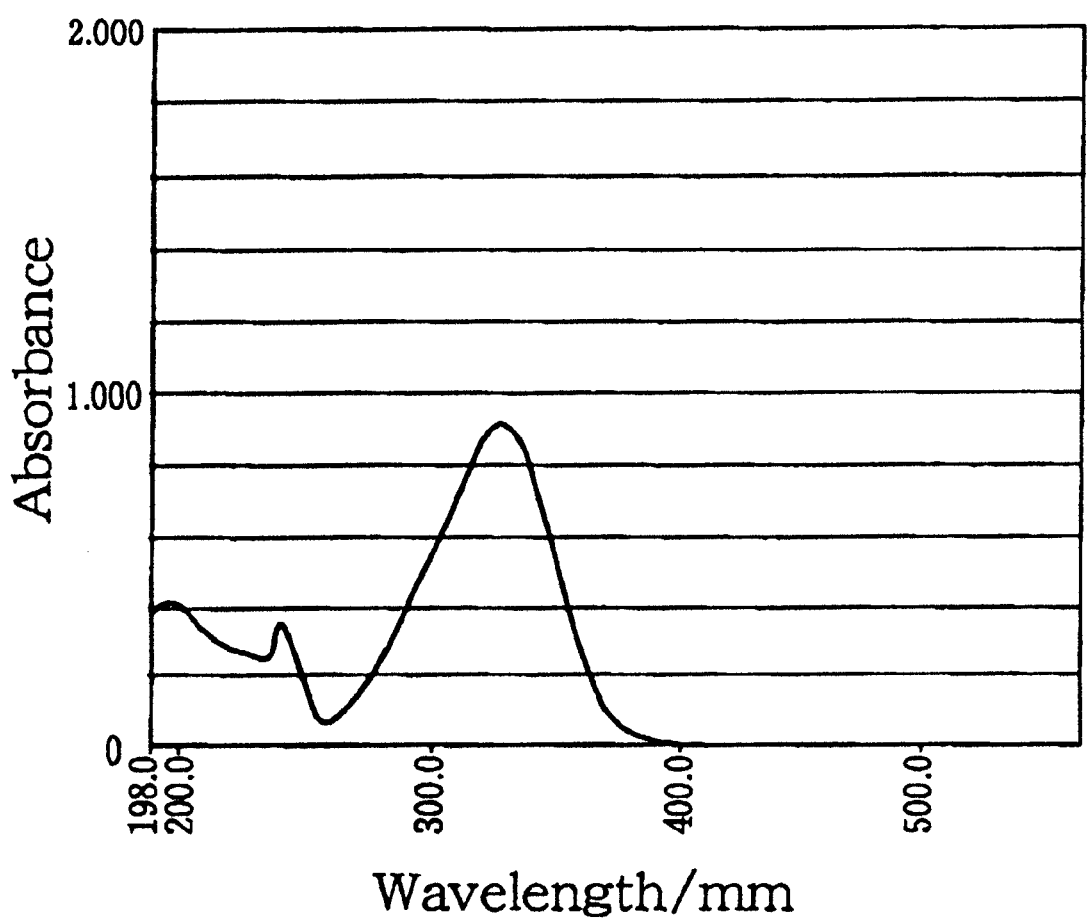
FIG. 2 is a ultraviolet·visible spectrum band chart of the final product.

Also, the final product was dissolved in chloroform and the ultraviolet-visible light absorption spectrum was measured. The results are shown in FIG. 2. It was confirmed from FIG. 2 that the final product had no absorption peaks in the visible light region, while on the other hand, it had the absorption peaks at 327 nm in the ultraviolet light region. It was found from this fact that the chemical adsorption material synthesized in this Example was low in sensitivity to visible light and high in sensitivity to ultraviolet light.

It is to be noted that in the following Examples, R-1200 available from Hitachi, Ltd. was used in the analysis of $^1$H-NMR spectrum; FTIR 4300 available from Shimadzu Corporation was used in the analysis of IR spectrum; and UV-240 available from Shimadzu Corporation was used in the analysis of UV/VIS spectrum.

[Confirmatory reaction for velation]

For the study of the coating film forming capabilities of the chemical adsorption material and the properties of the coating film formed, a coating film was actually formed on the glass substrate. The coating film was formed by the following process. The glass substrate was immersed in the solution of the above-said chemical adsorption material being dissolved in a ⅕ mixed solution of xylene/KF96L (available from Shin-Etsu Chemical Co., Ltd). To a concentration of 0.5 weight %, for about 2 hours. Thereafter, the substrate was taken out from the solution and its surface was fully washed by using chloroform in upstanding position to remove unreacted chemical adsorption material therefrom. Further, it was dried under air. The thin film was formed in this manner.

When contact angle of the thin film to the water was measured, it was 94 degree. It was found from this that the thin film had an adequate water-repellent property. Also, when the film thickness of the thin film was measured with an ellipsometer (whose index of refraction was set at (1.45), it was about 2.5 nm. It was found from this fact that the thin film of a generally monomolecular layer form was formed.

[Relation between polarized irradiation and alignment of liquid crystals]

The thin film produced in the same manner as in the above-mentioned thin film was subjected to the polarizing irradiation process: it was irradiated with polarized light (wavelength: 312 nm, light intensity: 2.1 mW/cm$^2$) as adjusted by use of a polarizing plate. Then, analysis was made on the film before and after the irradiation of polarized light by using FT-IR (Fourier Transform Infrared Spectroscopy). As a result of this, it was found that the polarized irradiation caused the molecules to be cross-linked to each other by the carbon—carbon double bond (—CH=CH—) expressed by the chemical formula (1–6) given above.

In addition, when the UV/VIS measurement was made of the thin film it was found that the 327 nm absorption, which had existed before the irradiation, disappeared after the irradiation. This indicates that the conjugated bond of the chalcone skeleton was cut and was varied into cross-link structure.

On the other hand, a liquid crystal cell (hereinafter it is called the test cell) was prepared in the manner that a substrate with a polarized light irradiated thin film is laid over another glass substrate with a gap of about 12 μm therebetween with its liquid thin film facing inwards and sealed around the margins thereof and, thereafter, nematic liquid crystal (available from Merck Industrial Chemicals, Brand name: ZL14792) is injected in the gap. Then, polarizing plates were arranged on both outside surfaces of the test cell, respectively. Then, the measurement was made of the capabilities of the thin film to align the liquid crystals by using visible light. It was confirmed from the measurement that the liquid crystal molecules in the cell are aligned uniformly in a certain direction.

Further, the surface of the substrate irradiated with the polarized light (the surface on the side opposite to the thin-film forming surface) was subjected to the rubbing. After the same surface of the substrate was heated at about 200° C. for 1 hour. The liquid crystal cell was built up. Then, the measurement was made again on the orientation of liquid crystal molecules. It was confirmed from the measurement that the orientation of the liquid crystal molecules was not varied by those outside stimulus.

It should be noted that the orientation of liquid crystals can be ascertained by the method of observing the polarized light (visible light) entering the test cell through the polarizing plate laid over one side of the test cell and passing through the cell in many directions.

SECOND INVENTIVE GROUP

An embodiment of the present invention will be described with reference to Examples.

EXAMPLE 2-1

First, the process for synthesizing the novel chemical adsorption material used in this example will be described.

(1) Synthesis of chemical adsorption material

The chemical adsorption material (silane-baced chemical adsorption material) synthesized in the following is the compound expressed by the chemical formula (2-3) given below.

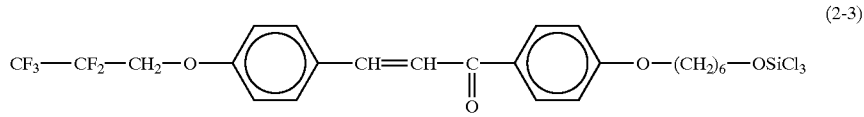

(2-3)

Reaction process 1:

1,675 ml of Sodium hydride (60%) and HMPA (hexamethylphosphoramide) was charged with a reaction flask (internal volume: 5L) and was cooled by freezing. Then, 380 g (2.53 mol) of 1H,1H-pentafluoropropanol was dropped into it at 15° C. or less for 3 hours. Thereafter, the reaction flask was restored to room temperature and the charged compound was agitated for 1 hour under the room temperature.

Then, after the mixture was cooled down to 10° C. or less, 209.4 g (1.69 mol) of p-fluorobenzaldehyde was dropped into the mixture for 1 hour. Thereafter, it was agitated at the same temperature for 3 hours.

The reactant thus obtained was poured into 3.4L of a 5% hydrochloric acid to extract the reaction product by using ethyl acetate and rinse it by using dilute hydrochloric acid. Then, the reaction product was dried by using magnesium sulfate anhydride and thereafter the solvent was distilled off to obtain crude crystals. The crude crystals thus obtained were purified by use of silica gel column (Moving phase:

n-hexane/ethyl acetate=10/1) to obtain 330.0 g of 4-(2,2,3,3,3-pentafluoropropyloxy) benzaldehyde (GLC purity: 95%, Yield: 76.9%).

(2-4)

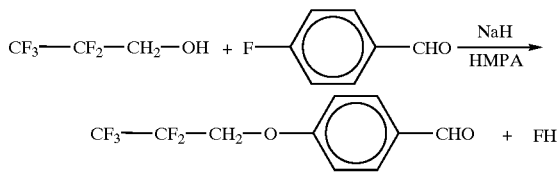

Reaction process 2:

330 g (1.30 mol) of 4-(2,2,3,3,3-pentafluoropropyloxy) benzaldehyde, 176.7 g (1.30 mol) of 4-hydroxyacetophenone, 33.0 g of piperidine, 33 ml of acetic acid and 3.3L of toluene were charged with the reaction flask (internal volume: 5L) and agitated at 110° C. for 5 days.

After the reaction flask was cooled down to room temperature, the reaction solution was poured into 2.1L of 1N hydrochloric acid and the deposited crystals were taken out by filtration.

Then, after the crystals were washed by water, they were dissolved in 15L of chloroform. Then, they were dried by using magnesium sulfate anhydride and, thereafter, the solvent was distilled off, to obtain 322.0 g of 4-(2,2,3,3,3-pentafluoropropyloxy)-4'-hydroxychalcone (GLC purity: 98% Yield: 66.6%).

The chemical reaction formula (2–5) in this process is given below.

(2-5)

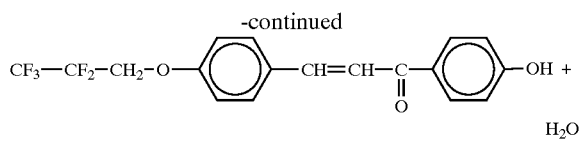

Reaction process 3:

322 g (0.866 mol) of 4-(2,2,3,3,3-pentafluoropropyloxy)-4'-hydroxychalcone and 3L of dry DMF were charged with the reaction flask (internal volume: 5L) in a stream of argon and 34.6 g (0.865 mol) of sodium hydride (60%) was added thereto under freezing for 30 minutes. Thereafter, the reaction flask was heated up to room temperature, the reactant was agitated for 20 hours.

Then, 117.7 g (0.865 mol) of 6-chlorohexanol was dropped into the mixture at the same temperature for 20 minutes and, thereafter, the reactant was heated to 80° C. to be allowed to react for 23 hours. Then, reaction solution was poured into ice water to extract the reaction product by using ethyl acetate. The solution was washed by water and then magnesium sulfate was added into the ethyl acetate extracted solution for treatment of it. Thereafter, the solvent was distilled off to obtain crude crystals.

The crude crystals thus obtained were purified by use of silica gel column (Moving phase: n-hexane/ethyl acetate= 2/1). Further, they were recrystallized by purifying them in silica gel column (Moving phase: n-hexane/ethyl acetate= 1/1) to obtain 123.0 g of 4-(2,2,3,3,3-pentafluoropropyloxy)-4'-(6'-hydroxyhexyloxy) chalcone (HPLC purity: 98%, Yield: 30%).

The chemical reaction formula (2–6) in this process is given below.

(2-6)

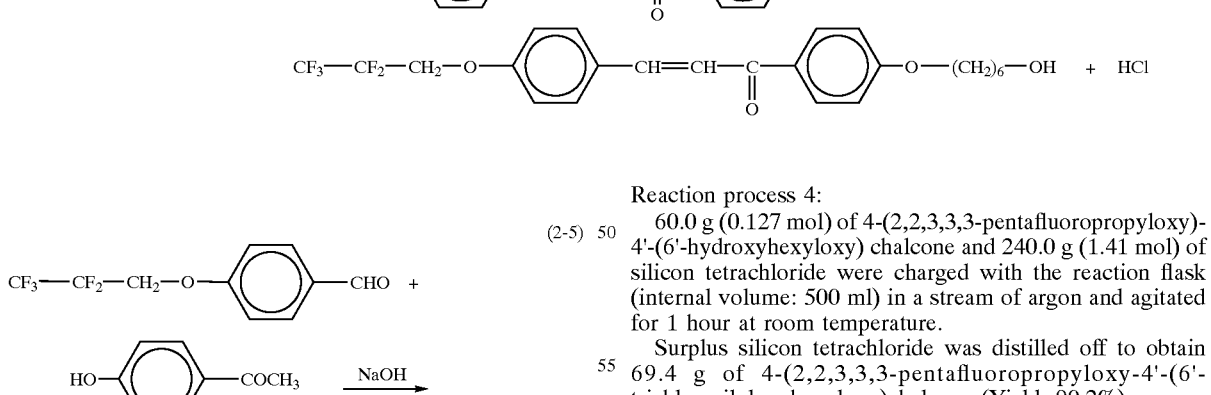

Reaction process 4:

60.0 g (0.127 mol) of 4-(2,2,3,3,3-pentafluoropropyloxy)-4'-(6'-hydroxyhexyloxy) chalcone and 240.0 g (1.41 mol) of silicon tetrachloride were charged with the reaction flask (internal volume: 500 ml) in a stream of argon and agitated for 1 hour at room temperature.

Surplus silicon tetrachloride was distilled off to obtain 69.4 g of 4-(2,2,3,3,3-pentafluoropropyloxy-4'-(6'-trichlorosilyloxyhexyloxy)chalcone (Yield: 90.2%).

The chemical reaction formula (2–7) in this process is given below.

(2-7)

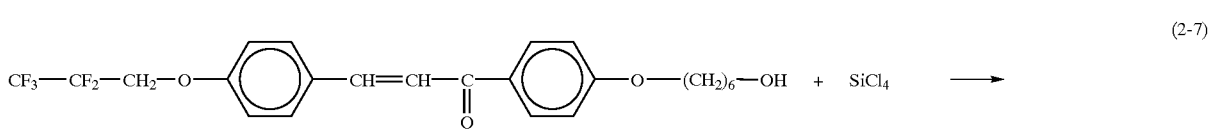

-continued

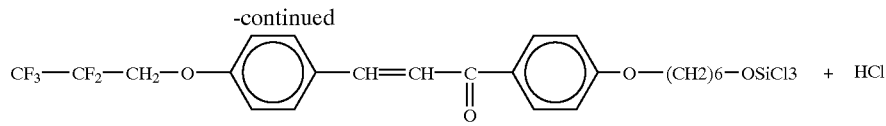

Figure 3:
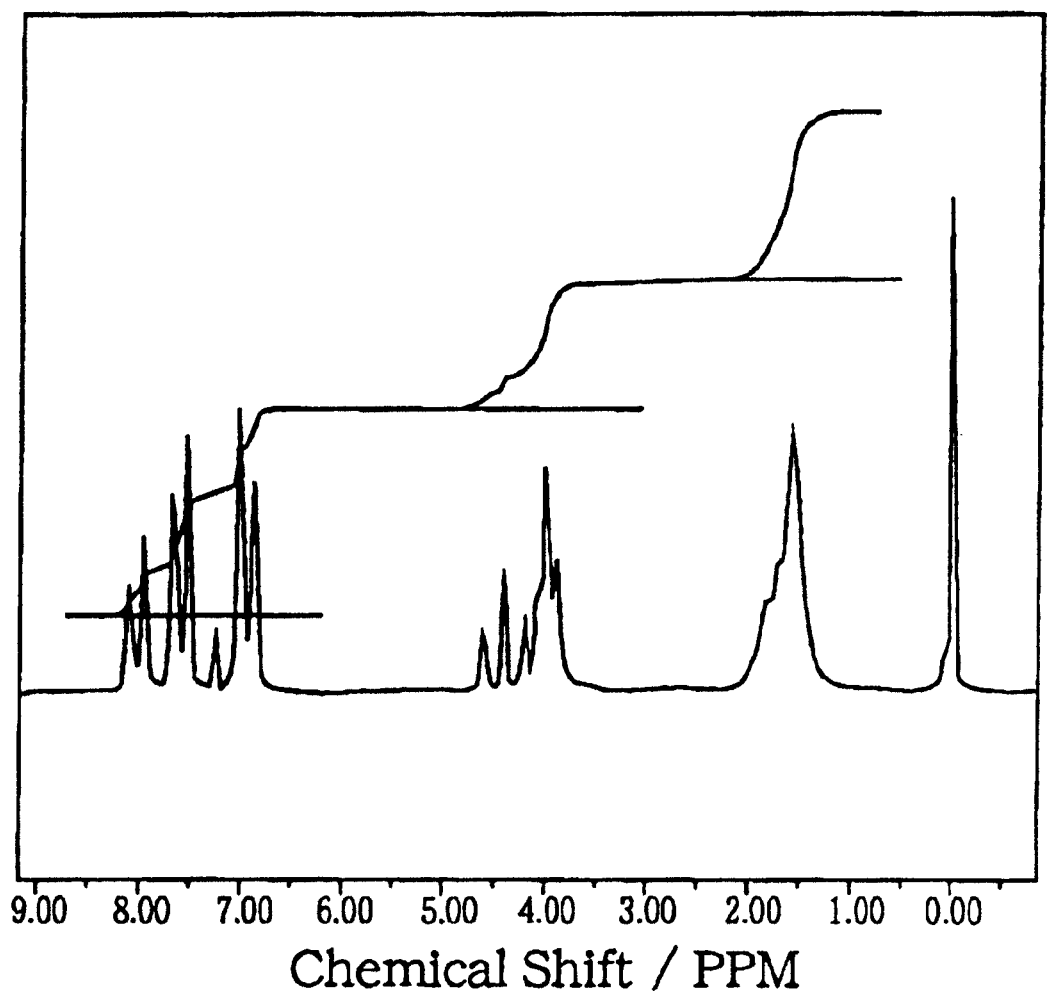
FIG. 3 is a $^1$H-NMR spectrum chart of the final product synthesized in Example 2-1 according to the second inventive group.

The final product was analyzed by measuring $^1$H-NMR spectrum. The $^1$H-NMR spectrum is shown in FIG. 3. The peaks in FIG. 3 support that the final product has the chemical structure expressed by the chemical formula (2–7) above.

Figure 4:
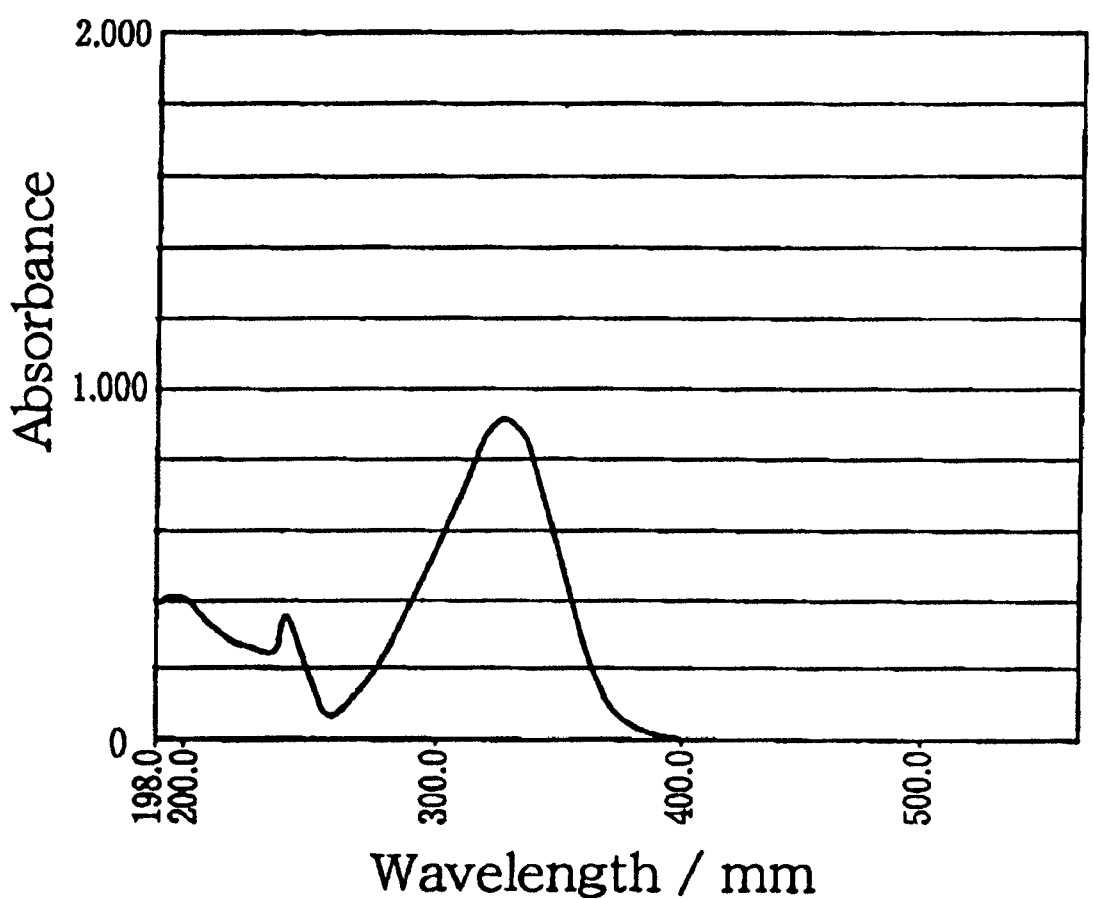
FIG. 4 is a ultraviolet·visible spectrum band chart of the final product.

Also, the final product was dissolved in chloroform and the ultraviolet·visible light absorption spectrum was measured. The results are shown in FIG. 4. It was confirmed from FIG. 4 that the final product had no absorption peaks in the visible light region, while on the other hand, it had the absorption peaks at 327 nm in the ultraviolet light region. It was found from this that the chemical adsorption material synthesized in this Example was low in sensitivity to visible light and high in sensitivity to ultraviolet light.

It is to be noted that in the following Examples, R-1200 available from Hitachi, Ltd. was used in the analysis of $^1$H-NMR spectrum; FT-IR 4300 available from Shimadzu Corporation was used in the analysis of IR spectrum; and UV-240 available from Shimadzu Corporation was used in the analysis of UV/VIS spectrum.

(2) Production of liquid crystal alignment film

The method for producing the liquid crystal alignment film will be described with reference to FIGS. 5 and 6. The surface of the glass substrate (including a number of hydroxyl groups) forming transparent electrodes thereon was well cleaned to remove grease to thereby finish the glass substrate 1. On the other hand, the (silane-based) chemical adsorption material synthesized in the above was dissolved in the mixed solvent of the well-dehydrated siloxane solvent (Brand name: KF96L, available from Shin-Estu Chemical Co., Ltd.) and chloroform to a concentration of about 1 weight %. The solution was regarded as chemical adsorption solution 2.

Figure 5:
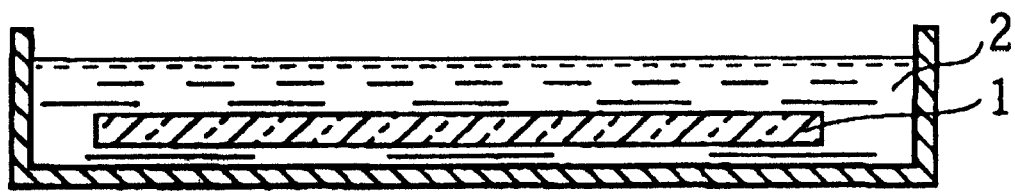
FIG. 5 is a conceptual diagram for explaining a chemical adsorption process.
Figure 6:
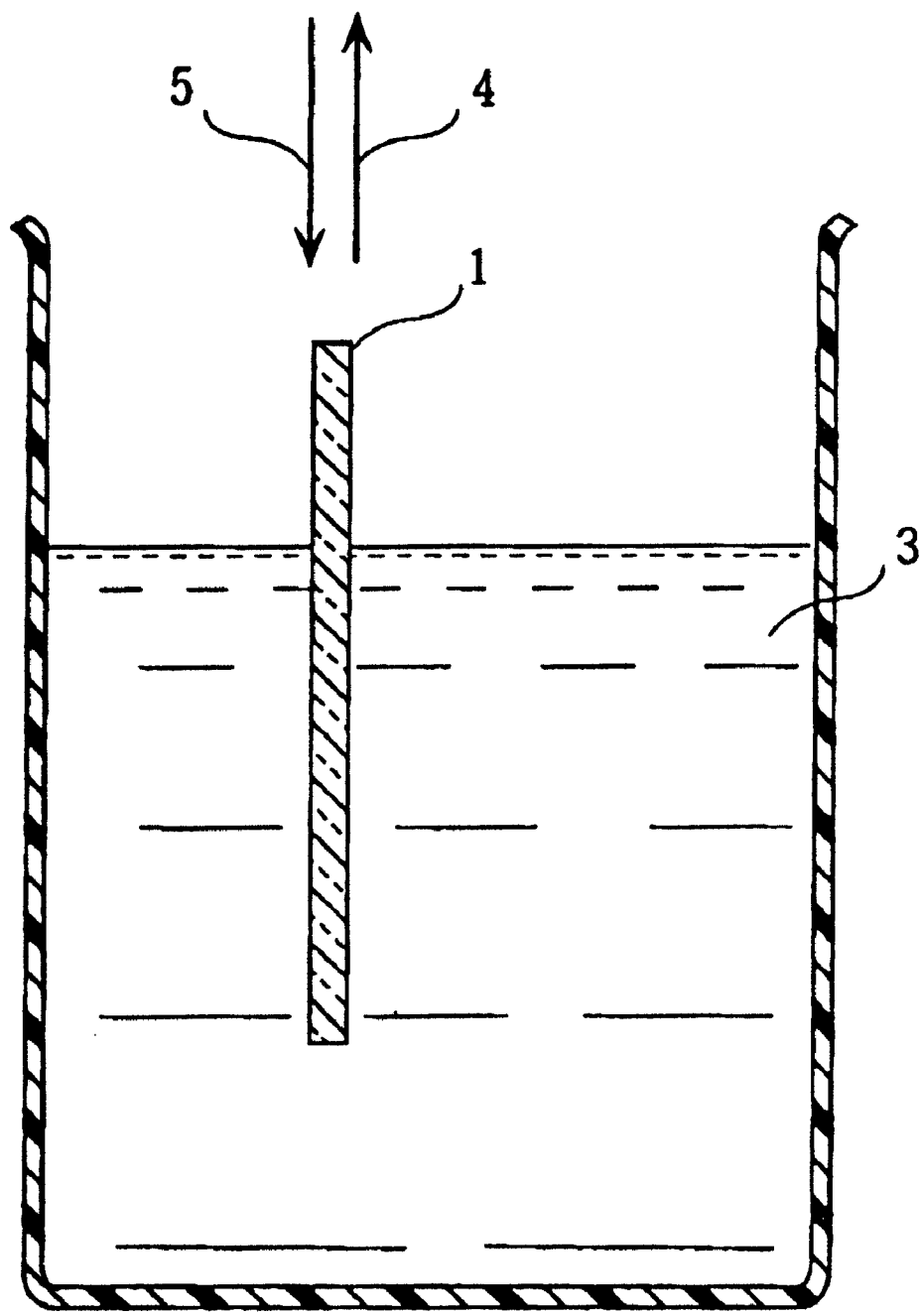
FIG. 6 is a conceptual diagram for explaining a cleaning process.
Figure 7:
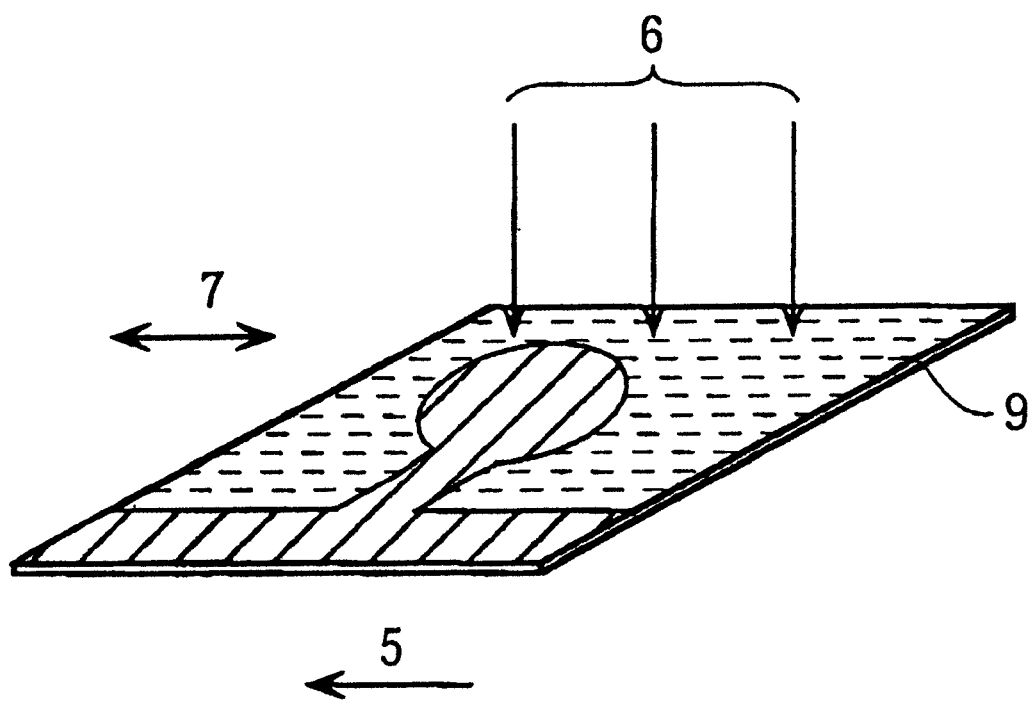
FIG. 7 is a conceptual diagram for explaining an irradiation process of polarized ultraviolet light.

Then, the glass substrate 1 was immersed in the chemical adsorption solution 2 in a dry atmosphere of relative humidity of 30% or less for about 1 hour, as shown in FIG. 5 (Process A). Thereafter, the glass substrate 1 was immersed in and taken out from the well-dehydrated chloroform 3 (aprotic solved) to rinse the surface of the substrate, as shown in FIG. 7 (Process B). Thereafter, the glass substrate 1 was pulled up in the direction of an arrow 4 from the chemical adsorption solution 2 and then was stood upright to cut the cleaning solution, so as to be dried (Process C). Sequentially, the surface of the glass substrate 1 was exposed to the air charged with moisture (relative humidity of 50–80%) (Process D).

The significance of the processes above is as follows. The process A in which the glass substrate 1 is immersed in the chemical adsorption solution 2 is for a SiCl group of chlorosilane chemical adsorption material and a hydroxyl group on the substrate to be subjected to de-HCl reaction. This process permits the chlorosilane chemical adsorption material to be strongly bonded to the surface of the glass substrate 1. The process B in which the glass substrate 1 pulled up from the chemical adsorption solution 2 is cleaned by the chloroform 3 is for removing the unreacted chemical adsorption material from the surface of the substrate. This process is necessary for forming the thin film of monomolecular layer form.

The cleaning solution draining and drying process after cleansing (Process C) is for allowing the adsorbing molecules to be aligned in a fixed direction. When the substrate is set up orienting in a fixed direction to cut and dry the cleaning solution remaining on the thin film of the substrate, the adsorption molecules are tentatively aligned along the draining and drying direction. After the glass substrate 1 is pulled up from the chemical adsorption solution after rinsing, it is set up vertically as it stands in the direction indicated by the arrow 5 in FIG. 6.

The process D in which the substrate dried after the cleaning solution is cut is exposed to the air charged with moisture is the de-HCl reaction process to allow the remaining Cl of the SiCl group to react with the moisture in the air. This process permits the siloxane bond of the adsorption molecules.

Through these series of processes, the monomolecular film 9 is formed which comprises chlorosilane chemical adsorption material siloxane-bonded to the hydroxyl groups on the substrate (in a tentatively aligned state). The monomolecular film 9 is a thin film in the monomolecular layer form which is formed as a unit of the chemical bond given by the following chemical formula (2–8). In place of the process for the glass substrate 1 to be immersed in the chemical adsorption solution 2, an alternative process may be adopted of applying the chemical adsorption solution 2 to the surface of the glass substrate 1.

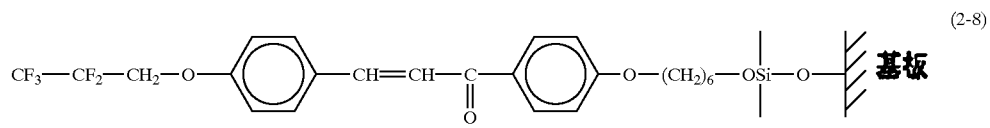

(2-8)

When the film thickness of the monomolecular film 9 thus produced was measured with an ellipsometer (whose index of refraction was set at 1.45), it was about 2.5 nm.

The alignment condition of the monomolecular film 9 was examined by means of the test cell. The test cell was produced in the following manner. Two substrates with monomolecular films 9 were produced. Then, they were superimposed with each other with a gap of about 12 μm in the condition in which their respective film surfaces face inwards and their respective film surfaces are so oriented that their solution draining directions are opposite to each other (in the anti-parallel condition) and then were sealed around the margins thereof. Thereafter, nematic liquid crystal (Δε of about −2 Δn of about 0.08) was injected in the gap and then the polarizing plates were arranged on both sides of the test cell, respectively. Then, the orientation of liquid crystal molecules was examined by the method that the visible light ray entering the polarizing plate from one direction is observed at many directions. It was confirmed from the measurement that the liquid crystal molecules were aligned along the solution draining and drying direction.

[Polarized light irradiation process]

The polarized light irradiation process will be described with reference to FIG. 7. In FIG. 7, 5 designates the solution draining and drying direction, 6 designates a polarized ultraviolet light, 7 designates a polarizing direction, 8 designates transparent electrodes, and 9 designates an aggregation of adsorption molecules (monomolecular film). The monomolecular film 9 was subjected to the re-alignment process in the manner as shown in FIG. 7. Specifically, after a Glan-Tayler type polarizer was so set that the polarizing direction 6 can be oriented in the direction generally parallel to the solution draining and drying direction 5 with respect to the monomolecular film 9, the monomolecular film 9 was irradiated with 480 mJ of a 365 nm ultraviolet 8 of a 500W high-pressure mercury lamp (2.1 mW/cm$^2$ after passing through the polarizing film).

Then, the chemical properties of the monomolecular film 9 as irradiated with the ultraviolet rays 8 was examined by use of FT-IR (Fourier Transform Infrared Spectroscopy). As a result of this, it was found that there was difference in IR absorption between the polarizing direction and the direction orthogonal thereto. Specifically, it was found that the IR absorption was significantly reduced in the polarizing direction, rather than in the direction orthogonal to the polarizing direction. The reduction of the IR absorption means that the chalcone skeleton was cross-linked at its carbon—carbon double bond portion by the optical energy in the polarizing direction. Hence, it was confirmed from this result that the irradiation of the polarized ultraviolet light enables the cross-link.

Though the direction for the molecules to be bonded to each other was not clarified by the FT-IR analysis, it is apparent that when the adsorption molecules are cross-linked to each other, the relation between the adsorption molecules is sterically stabilized. Consequently, the monomolecular film after the re-alignment process (liquid crystal alignment film) is probably more stable in alignment of liquid crystals than in the tentatively aligned state.

Also, the liquid crystal cell was produced in the same manner as in the above-mentioned test cell by use of the substrate with the liquid crystal alignment film as was re-aligned. Then, it was put to the liquid crystal alignment test. The result was that when no voltage was applied to the liquid crystal cell, the light was hindered from transmitting through the cell to thereby produce the black display, while on the other hand, when the voltage of 3 volts was applied thereto, the light was permitted to transmit therethrough to thereby produce the white display. This means that the alignment of the liquid crystal molecules was converted into the homogeneous alignment from the homeotropic alignment through the application of voltage. Further, when the pretilt angle was measured by the magnetic field threshold method, it was confirmed that the liquid crystal molecules were aligned at the pretilt angle of about 89.5 degree.

It was confirmed from these results that when the aggregation of adsorption molecules having the chemical bond units expressed by the chemical formula (1–8) above was subjected to the re-alignment process involving the cross link, in addition to the tentative alignment process, a ultrathin liquid crystal alignment film that can provide the high contrast ratio display by switching the voltage to ON and OFF was realized. It was also confirmed that in this liquid crystal alignment film, the adsorption molecules were cross-linked to each other. Consequently, the alignment characteristic is hard to deteriorate.

EXAMPLE 2-2

Figure 8:
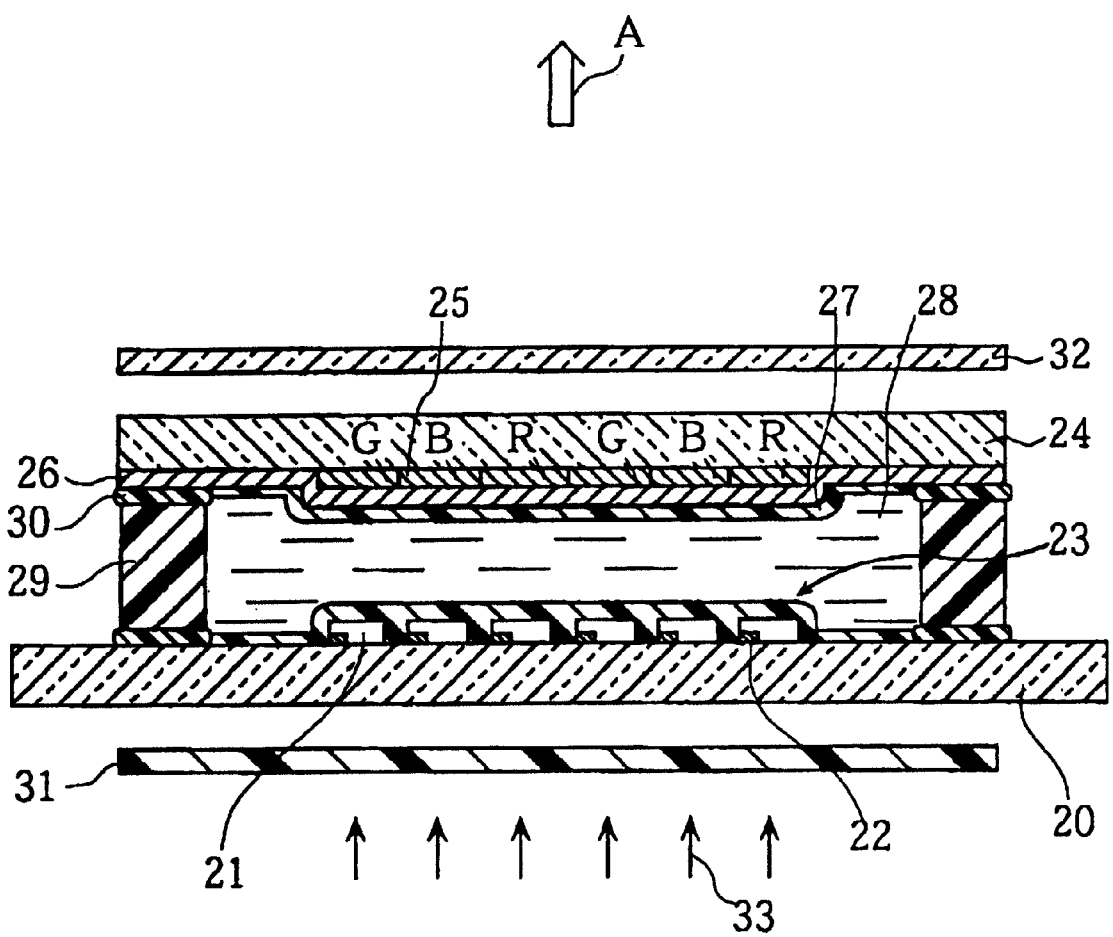
FIG. 8 is a sectional view schematically showing a section of the liquid crystal display according to Example 2-2 according to the second inventive group.

In Example 2-2, the substrate on which the pixel electrodes were arrayed in a matrix form was used, and the liquid crystal alignment film was formed on the substrate in the same manner as in Example 2-1. This substrate with the liquid crystal alignment film was used to produce a liquid crystal display. In the following, the producing process of the liquid crystal display of Example 2-2 will be described with reference to FIG. 8.

The chemical adsorption solutions which were prepared in the same manner as in Example 2-1 were made to contact with (i) a first substrate 23 having thereon a first group of transparent electrodes 21 arranged in a matrix form and a group of transistors 22 to drive the first group of electrodes and (ii) a second substrate 26 having thereon a group of color filters 24 and a second group of transparent electrodes 25 (common electrodes), respectively. Further, they are subjected to a series of processes of the solution draining and drying process and the polarized irradiation process to thereby produce the substrates 23, 26 with liquid crystal alignment films.

When the alignment properties of the alignment films of the substrates 23, 26 with liquid crystal alignment films were examined in the same manner as in Example 2-1, it was found that the liquid crystal alignment film 27 in which the liquid crystals were re-aligned along the electrode pattern was produced. Then, the substrates 23, 26 with liquid crystal alignment films were adapted to render the alignment of the liquid crystal alignment film homeotropic. Then, they were superimposed with each other, with a cell gap of 4.5 μm formed between the substrates by spacer 28 and adhesive 29, to thereby produce the liquid crystal cell.

Sequentially, nematic liquid crystal (Δε of about −3 and Δn of about 0.09) 30 was injected in the cell gap and the cell was fully sealed. Thereafter, the polarizing plates 31, 32 were combined with the cell to complete the liquid crystal display.

When the pretilt angle of the liquid crystal molecules in the liquid crystal display was measured by the magnetic field threshold method, it was about 89.8 degree. When the liquid crystal display was driven by video signals, while the liquid crystal display was irradiated with backlight 33 from the back thereof, it was confirmed that it could display a clear picture with respect to the direction of arrow A.

EXAMPLE 2-3

The liquid crystal alignment film was formed on the substrate in the same manner as in Example 2-2, except that the chemical adsorption material used was a mixed solution formed by phenyltrichlorosilane and fluorochemical adsorption material used in Example 1 (4-(2,2,3,3,3,-Pentafluoropropyloxy)-4'-(6'-trichlorosilyloxyhexyloxy) chalcone) being mixed at a mixing ratio of 9:1.

The liquid crystal alignment film thus produced was measured on the pretilt angle of the liquid crystal molecules by the crystal rotation method. The result was that the pretilt angle was 8.5 degree.

Further, the liquid crystal display was produced in the same manner as in Example 2-2. The liquid crystal material used was nematic liquid crystal whose Δε was about 2.3 and Δn was about 0.26. Further, when the liquid crystal display was driven by use of video signals, while the liquid crystal display was irradiated with backlight from the back thereof, it was confirmed that it could display a clear picture.

It was confirmed from this fact that the liquid crystal alignment film having good controllability of alignment of liquid crystals and having the capabilities of controlling the liquid crystals at a desired pretilt angle and displaying clear picture could be provided by mixing the two different chemical adsorption materials.

EXAMPLE 2-4

In the irradiation of polarized ultraviolet light after the tentative alignment, a pattern-like mask for dividing each picture element into four regions in a checkered pattern was laid over the polarizing plate and then was exposed to light at one time, to thereby produce a multi-domain type liquid crystal alignment film having four divided regions different in orientation for the liquid crystals to be aligned in patterns within the same picture element. Except this condition, the multi-domain type liquid crystal display according to Example 2-4 was produced in the same conditions as in Example 2-2.

When the liquid crystal display was driven by use of video signals in the same manner as in Example 2-2, it was confirmed that it could display a picture of a wide viewing angle, as compared with the case of Example 2-2.

EXAMPLE 2-5

The two comb electrodes meshed with each other in a non-contact state were disposed on the same plane of a single substrate and then the liquid crystal alignment film as was subjected to the re-alignment process was further formed on those electrodes in the same manner as in Example 1. However, the chemical adsorption solution used was a mixed solution formed by fluorochemical adsorption material synthesized in Example 1 (4-(2,2,3,3,3,-Pentafluoropropyloxy)-4'-(6'-trichlorosilyloxyhexyloxy) chalcone) and the chemical adsorption material in which the fluorine was not contained in the fluorochemical adsorption material synthesized in Example 1 being mixed at a mixing ratio of 1:29. The opposite substrate was superimposed with the substrate with the liquid crystal alignment film to form the liquid crystal cell in the usual way to thereby produce an in-plane switching (IPS) mode of liquid crystal display.

In the liquid crystal display also, the picture display test was conducted by using video signals in the same manner as in Example 2-2 or Example 2-4. It was confirmed from this test that the picture was displayed with an expanded viewing angle.

OTHER RESPECTS (1) While the liquid crystal alignment films were formed on the pair of opposed substrates in Example 2-2 to Example 2-4, the liquid crystal alignment film may merely be formed on either substrate. However, when the liquid crystal alignment film according to the present invention is formed on each of the pair of opposed substrates, further improved alignment stability can be provided.

(2) While 365 nm of the light of the high-pressure mercury lamp was used as the polarized ultraviolet light in Example 2-1 through Example 2-5, the wavelengths of light that may be used is not limited to this. Since the novel chemical adsorption material shown in the chemical formula (2-1) has a large absorption width in the ultraviolet range, as shown in FIG. 4, a variety of ultraviolet lights may be used. For example, the wavelengths of ultraviolet light that may be used include 436 nm, 405 nm and 254 nm, and 248 nm of the wavelength of light obtained by use of a KrF excimer laser. Of these wavelengths of light, 248 nm and 254 nm of lights that are easily absorbed in the chemical adsorption material are superior in terms of energy orientation efficiency.

(3) While Example 2-4 adopts the process that the pattern-like mask for dividing each picture element into four regions in a checkered pattern is laid over the polarizing plate and is exposed to light at one time, an alternative process may be adopted that the solution draining and drying process and the polarized ultraviolet irradiation process are repeated a number of times. Specifically, the following process may be adopted.

The solution draining and drying process performed at a N-th time (N is an integer number of 2 or more) is differentiated in solution draining and drying direction from the solution draining and drying process that has been performed until the (N–1)-th time and also the polarized ultraviolet irradiation process performed at a N-th time, which is performed following the solution draining and drying process at the N-th time, is differentiated in irradiation region from the polarized ultraviolet irradiation process that has been performed until the (N–1)-th time. This can allow the tilt of the major axes of the thin-film constituent molecules with respect to the substrate and/or the orientation of alignment of the molecules to vary in each of the patterned regions of the alignment film into which the section corresponding to one picture element was divided. Another alternative may be adopted that only the irradiation region of the polarized ultraviolet light is varied and the irradiation is repeated a number of times. However, the process that the solution draining and drying process and the polarized ultraviolet irradiation process are repeated a number of times can facilitate the control of the orientation of cross-link reaction to produce the alignment film excellent in alignment characteristic and alignment stability.

(4) While the anhydrous chloroform was used as cleansing solvent in Examples 2-1 through 2-5, the cleansing solvents that may be used are not limited to this. In addition to this, various kinds of solvents that contain no water and dissolve the chemical adsorption material may be used. For example, aprotic solvents that may be used include chlorine solvents such as chloroform, aromatic solvents such as benzene and toluene, lactonic solvents such as γ-butyl lactone, and ester solvents such as ethyl acetate. Also, protic solvents that may be used include alcoholic solvents such as methanol and ethanol.

(5) The liquid crystals that may be used in the liquid crystal display of the present invention include nematic liquid crystal, smectic liquid crystal, discotic liquid crystal and ferroelectric liquid crystal. Nematic liquid crystal is preferably used particularly in the aspect of its molecular form. The nematic liquid crystals include, for example, biphenyl, tarphenyl, azoxy, Schiff base, phenylcyclohexane, biphenylcyclohexane, ester, pyrimidine, dioxane, bicyclooctane, and cubane.

(6) While in Examples 2-1 through 2-5, the aggregation of adsorption molecules (thin film) was formed on the surface of the substrate by the process of bringing the chemical adsorption material into direct contact with the surface of the substrate having the electrodes, it may be formed by an alternative process that a ground layer having hydrophilic groups (another material layer) is formed in advance on the surface of the substrate having the electrodes, via which the chemical adsorption material is chemically bonded to the surface of the substrate. This alternative process is effective for the substrate having a few hydrophilic groups thereon. The ground layers that may be used include the layers having thereon hydrophilic groups such as a OH group, a COOH group, a $NH_2$ group, a NH group and a SH group. To be more specific, a $SiO_2$ layer and $TiO_2$ layer may be used as the ground layer.

(7) In Examples 2-1 through 2-5, the alignment film having the capability of controlling the alignment of liquid crystal molecules at a desired pretilt angle may be formed by performing the following operations for the liquid crystal alignment film as was formed in the respective Examples. For example, when a part of liquid crystal alignment film formed in Example 2-3 is spot-irradiated with infrared light and then is annealed under the conditions of a heating temperature of 90° C. and a processing time of 30 minutes, a region for the liquid crystal molecules to be aligned at the pretilt angle of about 10.3 degree is formed in the liquid crystal alignment film at a part thereof. Further, under the conditions of the heating temperature of 150° C. and the processing time of 30 minutes, the region for the liquid crystal molecules to be aligned at the pretilt angle of about 11.5 degree is formed in the liquid crystal alignment film at a part thereof.

To achieve the control of the liquid crystal alignment capabilities of the liquid crystal alignment film, one is not limited to using the annealing process mentioned above. One can use another process that additional chemical adsorption material having a different affinity to the liquid crystal from the chemical adsorption material synthesized in Example 2-1 is added and a mixing ratio between the both is varied variously. Further, one can use still another process that kinds of cleaning solutions used in the process for cleansing the substrate to which the chemical adsorption material is adsorbed (corresponding to the process B in Example 2-1) are varied.

It is to be understood that the specific embodiments described above are only for clarifying the technical contents of the present invention and the present invention should not be construed in such a narrow sense that it is limited to such concrete examples and that various changes and modifications may be made in the invention without departing from the sprit thereof and the scope of the following claims.

CAPABILITIES OF EXPLOITATION IN INDUSTRY

As described above, according to the construction of the present invention, the objects of the present invention can fully be achieved.

According to the first group of invention, the novel chemical adsorption material of the invention comprises a functional group having at one end thereof a functional group of very small critical surface tension and at the other end thereof a functional group capable of strong chemical bond to a hydrophilic group on the surface of the substrate, and a photosensitive group. Consequently, according to the present invention, a thin film of a monomolecular layer form can be formed on the surface of the base substance with ease. The thin film is stable and transparent in the visible light region and also excellent in water repellency and durability, so that it is useful as a functional coating film for modification of surface property.

Further, the chemical adsorption material of the present invention can allow the adsorption molecules to be cross-linked to each other in a specific direction by the process that the chemical adsorption material is chemically adsorbed to the surface of the base substance and thereafter is irradiated with polarized ultraviolet light. This can produce the liquid crystal alignment film having strong and stable alignment properties.

In addition, according to the producing method of chemical adsorption material of the present invention, the chemical adsorption material mentioned above can be produced with efficiency.

From the foregoing, according to the present invention, there is provided the novel thin-film forming chemical adsorption material that is useful as a surface property modifying agent for a base substance, or particularly useful as the material of the liquid crystal alignment film. Consequently, industrial significance of the present invention is great.

According to the second group of the invention, there is provided the liquid crystal alignment film of far small in thickness and uniform in alignment, as compared with the conventional organic polymer liquid crystal alignment film. Also, since the liquid crystal alignment film has the structure in which the adsorption molecules are strongly bonded and anchored on the surfaces of electrodes via the chemical adsorption and also are cross-linked to each other, it is excellent in adhesion to the substrate and also is resistant to deterioration of the alignment properties resulting from external factors such as heat and friction. Further, there exists a perfluoromethyl group at an end of the adsorption molecule on the front side of the film, and as such can produce the liquid crystal alignment film having a very large critical surface tension and can allow the liquid crystal molecules to be aligned to a high pretilt angle. Furthermore, since individual adsorption molecules are contributive to the control of alignment of liquid crystal molecules, far excellent alignment properties can be provided.

Further, the thin film of a monomolecular layer form comprising the aggregation of adsorption molecules has significantly advantageous properties as the liquid crystal alignment film that it does not hinder the transmission of light due to its excellent transmission of the visible light and that it does not hinder the electric field to drive the liquid crystals due to its small electrical resistance.

According to the producing method of the present invention, the multi-domain type liquid crystal alignment film of different in orientation for the liquid crystals to be aligned in each of the regions divided to a pattern can be reliably and efficiently produced by a relatively simple technique simply using the solution draining and drying process and the irradiation of polarized light. The applications of the liquid crystal alignment film according to the present invention can provide the homeotropic alignment mode of multi-domain type liquid crystal display having wide viewing angle, high picture quality, high contrast and excellent high-speed response with little increase of costs.

What is claimed is:

1. A thin film forming chemical adsorption material comprising at least a functional group expressed by the following chemical formula (1-1) and a —SiX group (X represents halogen) as an end group bonded by siloxane bond:

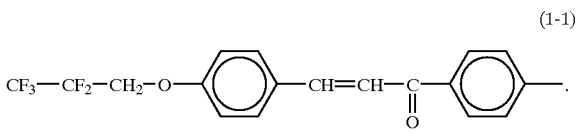

(1-1)

2. The thin film forming chemical adsorption material according to claim 1, wherein the chemical adsorption material is expressed by the following chemical formula (1-2):

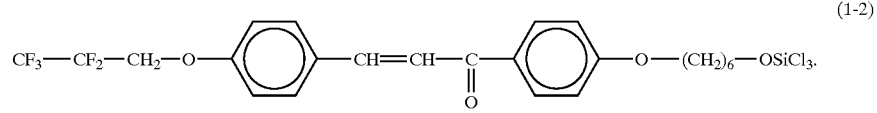

(1-2)

3. A producing method of a thin film forming chemical adsorption material comprising at least:

the chemical reaction process 1 that at least 4-(2,2,3,3,3-Pentafluoropropyloxy) benzaldehyde and 4-hydroxyacetophenone are subjected to aldol condensation reaction to synthesize alcohol having a chalcone skeleton expressed by the following chemical formula (1-3) (chemical reaction process 1); and the chemical reaction process 2 that after the chemical reaction process 1, $SiX_4$ (X represents halogen) is subjected to dehydrohalogenation reaction with alcohol having the chalcone skeleton under an inert gas atmosphere, to synthesize chemical adsorption material having a characteristic group expressed by the following chemical formula (1-1) and a —O—$SiX_3$ group:

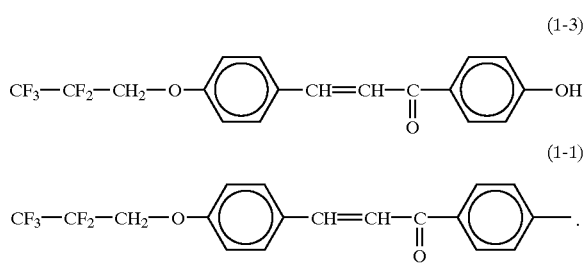

(1-3)

(1-1)

4. The producing method of a thin film forming chemical adsorption material according to claim 3, wherein the chemical adsorption material is a compound expressed by the following chemical formula (1-2):

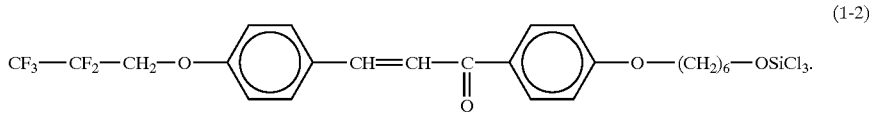

(1-2)

5. An organic thin film comprising an aggregation of adsorption molecules directly bonded and anchored to or indirectly bonded and anchored to a surface of a base substance through another material layer via chemical adsorption, wherein the aggregation of adsorption molecules include adsorption molecule having a characteristic group expressed by the following chemical formula (2-1) and a —O—Si bond group at a molecular end group:

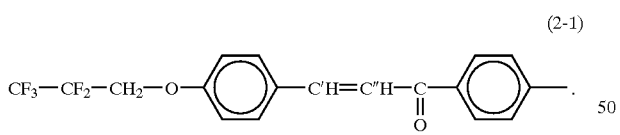

(2-1)

6. The organic thin film according to clam 5, wherein the adsorption molecule having the characteristic group expressed by the chemical formula (2-1) and the —O—Si bond group at the molecular end group is a compound expressed by the following chemical formula (2-2):

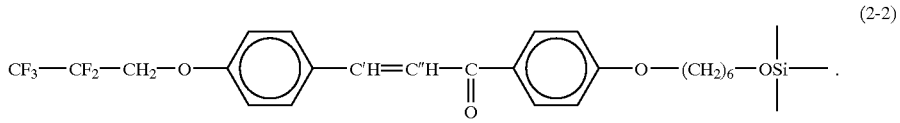

(2-2)

7. The organic thin film according to claim 5, wherein the aggregation of adsorption molecules forming the organic thin film are aligned in a given direction.

8. The organic thin film according to claim 5, wherein the aggregation of adsorption molecules forming the organic thin film are adsorbed on a substrate in such a manner that the adsorption molecules in adjoining divided regions are differentiated from each other in tilt of their major exes with respect to the surface of the substrate and/or in orientation of alignment thereof, and wherein the divided regions are formed by dividing a single picture element into a number of regions in a pattern-like form.

9. The organic thin film according to claim 5, wherein the aggregation of adsorption molecules forming the organic thin film are cross-linked to each other via a boning line(s) of C' and/or C" in the chemical formula (2-1) or (2-2).

10. The organic thin film according to claim 9, which has film thickness of 0.5 nm or more to less than 10 nm.

11. The organic thin film according to claim 9, which a thin film of a monomolecular layer form.

12. The organic thin film according to claim 5, wherein the organic thin film comprises an aggregation of adsorption molecules of various kinds.

13. A producing method of an organic thin film comprising an aggregation of adsorption molecules directly bonded and anchored to or indirectly bonded and anchored to a surface of a base substance through another material layer via chemical adsorption, the producing method comprising:

the process that chemical adsorption material having a characteristic group expressed by the following chemical formula (2-1) and a —O—Si bond group at a molecular end portion thereof is at least dissolved in non-water-borne solvent, to prepare chemical adsorption solution;

the process that the chemical adsorption solution is put into contact with the surface of the base substance, so that the chemical adsorption material in the chemical adsorption solution is chemically adsorbed on the surface of the base substrate; and the solution draining and drying process that the surface of the base substance to which the chemical adsorption material was bonded is cleaned by use of the non-water-borne solvent and, thereafter, the base substance is stood up in a specific direction to cut and dry the cleaning solution:

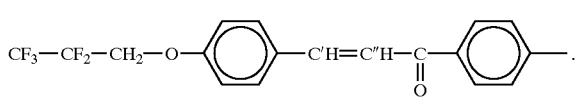
(2-1)

14. The producing method of an organic thin film according to claim 13, which further comprises the polarized ultraviolet irradiation process that after the solution draining and drying process, the adsorption molecules on the surface of the base substance are irradiated with polarized ultraviolet light, so that they are cross-linked to each other via a bonding line of a carbon-carbon double bond portion of the chemical formula (2-1).

15. The producing method of an organic thin film according to claim 14, wherein a series of alignment film treatment processes comprising the solution draining and the drying process and a polarized ultraviolet irradiation process are repeated a number of times in such a manner that the solution draining and drying process returns back again from the polarized ultraviolet irradiation process, and each time when repeated, the solution draining and drying direction is varied and that the polarized ultraviolet light irradiation region and polarized ultraviolet light irradiation direction, or the polarized ultraviolet light irradiation region and polarized ultraviolet light irradiation angle, or the polarized ultraviolet light irradiation region, polarized ultraviolet light irradiation direction and polarized ultraviolet light irradiation angle, are varied, whereby the adsorption molecules are varied in tilt of their major exes with respect to the surface of the base substance and/or in orientation of alignment thereof from one divided region to another of a number of divided regions into which a region corresponding to one picture element is divided in a pattern-like form.

16. The producing method of an organic thin film according to claim 13, wherein aprotic solvent is used as the non-water-borne solvent for use in cleaning, so that unreacted chemical adsorption material is cleaned and removed from the surface of the base substance by use of the aprotic solvent, to produce a thin film of a monomolecular layer form.

17. The producing method of an organic thin film according to claim 13, wherein a mixed solvent of aprotic solvent and protic solvent is used as the non-water-borne solvent for use in cleaning, so that unreacted chemical adsorption material is cleaned and removed from the surface of the base substance by use of the mixed solvent, to produce a thin film of a monomolecular layer form:

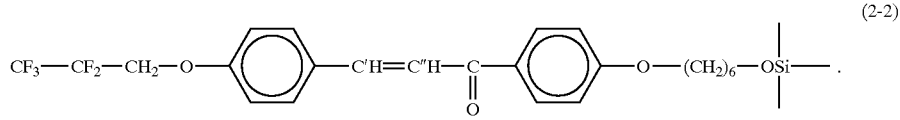
(2-2)

18. The producing method of an organic thin film according to claim 13, wherein the chemical adsorption material having a characteristic group expressed by the chemical formula (2-1) and a —O—Si bond group at a molecular end portion thereof is a compound expressed by the following chemical formula (2-2).

19. A liquid crystal alignment film comprising an aggregation of adsorption molecules bonded and anchored directly on a surface of a substrate forming electrodes thereon or indirectly bonded and anchored thereon through another material layer, wherein the aggregation of adsorption molecules include adsorption molecule having a characteristic group expressed by the following chemical formula (2-1) and a —O—Si bond group at a molecular end group:

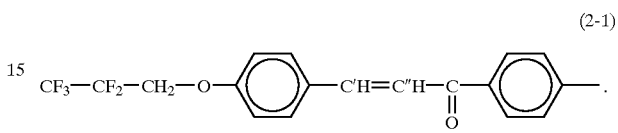
(2-1)

20. The liquid crystal alignment film according to claim 19, wherein the adsorption molecule having the characteristic group expressed by the chemical formula (2-1) and the —O—Si bond group at the molecular end group is a compound expressed by the following chemical formula (2-2):

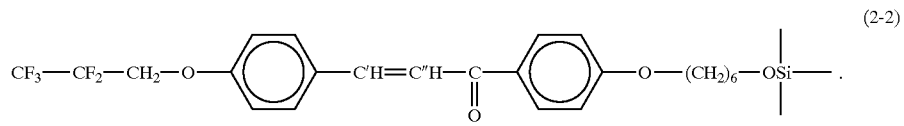
(2-2)

21. The liquid crystal alignment film according to claim 19, wherein the aggregation of adsorption molecules forming the liquid crystal alignment film are aligned in a given direction.

22. The liquid crystal alignment film according to claim 19, wherein the aggregation of adsorption molecules forming the liquid crystal alignment film are adsorbed on a substrate in such a manner that the adsorption molecules in adjoining divided regions are differentiated from each other in tilt of their major exes with respect to the surface of the substrate and/or in orientation of alignment thereof, and wherein the divided regions are formed by dividing a single picture element into a number of regions in a pattern-like form.

23. The liquid crystal alignment film according to claim 19, wherein the adsorption molecules forming the liquid crystal alignment film are cross-linked to each other via a boning line(s) of C' and/or C" in the chemical formula (2-1) or (2-2).

24. The liquid crystal alignment film according to claim 23, which has film thickness of 0.5 nm or more to less than 10 nm.

25. The liquid crystal alignment film according to claim 23, which is a thin film of a monomolecular layer form.

26. The liquid crystal alignment film according to claim 19, which is an alignment film that develops a desired pretilt angle for the liquid crystal molecules.

27. The liquid crystal alignment film according to claim 26, wherein the liquid crystal alignment film comprises the aggregation of adsorption molecules of various kinds, and the liquid crystal molecules are aligned at a desired pretilt angle by changing a constituent ratio between the various kinds of adsorption molecules.

28. A producing method of a liquid crystal alignment film comprising an aggregation of adsorption molecules directly bonded and anchored to or indirectly bonded and anchored to a surface of a substrate forming thereon electrodes through another material layer via chemical adsorption, the producing method comprising:

the process that chemical adsorption material having a characteristic group expressed by the following chemical formula (2-1) and a —O—Si bond group at a molecular end portion thereof is at least dissolved in non-water-borne solvent, to prepare chemical adsorption solution;

the process that the chemical adsorption solution is put into contact with the surface of the substrate forming the electrodes thereon, so that the chemical adsorption material in the chemical adsorption solution is chemically adsorbed on the surface of the substrate; and the solution draining and drying process that the surface of the substrate to which the chemical adsorption material was bonded is cleaned by use of the non-water-borne cleaning solvent and, thereafter, the substrate is stood up in a specific direction to cut and dry the cleaning solution:

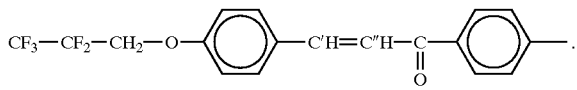

(2-1)

29. The producing method of the liquid crystal alignment film according to claim 28, which further comprises the polarized ultraviolet irradiation process that after the solution draining and drying process, the adsorption molecules on the surface of the substrate are irradiated with polarized ultraviolet light, so that they are cross-linked to each other via a bonding line of a carbon-carbon double bond portion of the chemical formula (2-1).

30. The producing method of the liquid crystal alignment film according to claim 28, wherein a series of alignment film treatment processes comprising the solution draining and the drying process and a polarized ultraviolet irradiation process are repeated a number of times in such a manner that the solution draining and drying process returns back again from the polarized ultraviolet irradiation process, and each time when repeated, the solution draining and drying direction is varied and that the polarized ultraviolet light irradiation region and polarized ultraviolet light irradiation direction, or the polarized ultraviolet light irradiation region and polarized ultraviolet light irradiation angle, or the polarized ultraviolet light irradiation region, polarized ultraviolet light irradiation direction and polarized ultraviolet light irradiation angle, are varied, whereby the adsorption molecules are varied in tilt of their major exes with respect to the surface of the substrate and/or in orientation of alignment thereof from one divided region to another of a number of divided regions into which a region corresponding to one picture element is divided in a pattern-like form.

31. The producing method of the liquid crystal alignment film according to claim 28, wherein aprotic solvent is used as the non-water-borne solvent for use in cleaning, so that unreacted chemical adsorption material is cleaned and removed from the surface of the substrate by use of the aprotic solvent, to produce a thin film of a monomolecular layer form.

32. The producing method of the liquid crystal alignment film according to claim 28, wherein a mixed solvent of aprotic solvent and protic solvent is used as the non-water-borne solvent for use in cleaning, so that unreacted chemical adsorption material is cleaned and removed from the surface of the substrate by use of the mixed solvent, to produce a thin film of a monomolecular layer form.

33. The producing method of the liquid crystal alignment film according to claim 28, wherein the chemical adsorption material having a characteristic group expressed by the chemical formula (2-1) and a —O—Si bond group at a molecular end portion thereof is a compound expressed by the following chemical formula (2-2):

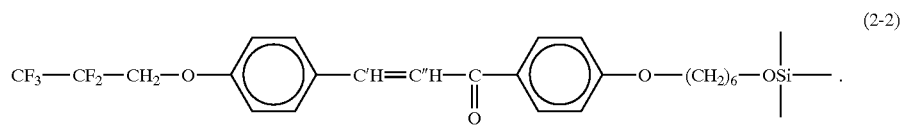

(2-2)

34. A liquid crystal display comprising:

a pair of opposed substrates;

a liquid crystal alignment film formed at least on a surface of a substrate having electrodes of the pair of substrates; and liquid crystals accommodated in a cell gap between the pair of opposed substrates, wherein the liquid crystal alignment film comprises an aggregation of adsorption molecules bonded and anchored directly on a surface of the substrate forming the electrodes thereon or indirectly bonded and anchored thereon through another material layer via chemical adsorption, and wherein the aggregation of adsorption molecules include adsorption molecule having a characteristic group expressed by the following chemical formula (2-1) and a —O—Si bond group at a molecular end group:

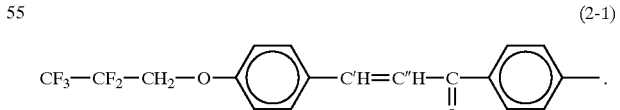

(2-1)

35. The liquid crystal display according to claim 34, wherein the adsorption molecule having the characteristic group expressed by the chemical formula (2-1) and the —O—Si bond group at the molecular end group is a compound expressed by the following chemical formula (2-2):

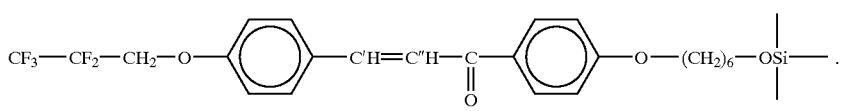

36. The liquid crystal display according to claim 34, wherein a pretilt angle and/or a pretilt orientation of the adsorption molecules accommodated in the cell gap are controlled by tilt and/or orientation of alignment of the adsorption molecules' major axes with respect to surface of the substrate.

37. The liquid crystal display according to claim 34, wherein the adsorption molecules are differentiated from each other in tilt and/or orientation of alignment of their major axes with respect to surface of the substrate from one divided region to another of adjoining divided regions into which a single picture element is divided in a pattern-like form.

38. The liquid crystal display according to claim 34, wherein the adsorption molecules forming the liquid crystal alignment film are cross-linked to each other via a boning line(s) of C' and/or C" in the chemical formula (2-1) or (2-2).

39. The liquid crystal display according to claim 34, wherein the liquid crystal alignment film has film thickness of 0.5 nm or more to less than 10 nm.

40. The liquid crystal display according to claim 34, wherein the liquid crystal alignment film is a thin film of a monomolecular layer form.

41. The liquid crystal display according to claim 34, wherein the liquid crystal alignment film is an alignment film that develops a desired pretilt angle for the liquid crystal molecules.

42. The liquid crystal display according to claim 41, wherein the liquid crystal alignment film comprises the aggregation of adsorption molecules of various kinds, and the liquid crystal molecules are aligned at a desired pretilt angle by changing a constituent ratio between the various kinds of adsorption molecules.

43. The liquid crystal display according to claim 42, whose display mode is a display mode selected from the group consisting of TN (Twisted Nematic) mode, STN (Super Twisted Nematic) mode, OCB (Optically Self-Compensated Birefringence) mode and VA (Vertical Alignment) mode.

44. An in-plane switching type liquid crystal display comprising pixel electrodes and opposed electrodes, which are arranged on a substrate, and a liquid crystal alignment film formed on a surface of the substrate on which the electrodes are arranged, wherein the liquid crystal alignment film comprises an aggregation of adsorption molecules bonded and anchored directly on a surface of the substrate forming the electrodes thereon or indirectly bonded and anchored thereon through another material layer via chemical adsorption, and wherein the aggregation of adsorption molecules include adsorption molecule having a characteristic group expressed by the following chemical formula (2-1) and a —O—Si bond group at a molecular end group:

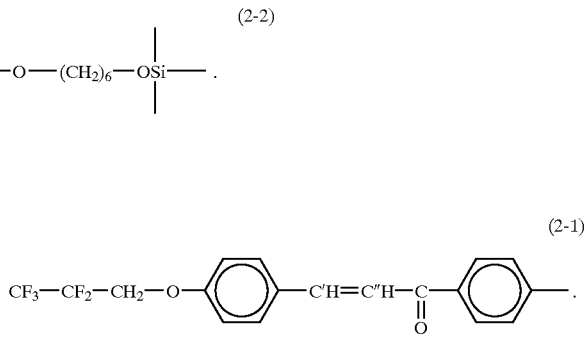

45. The liquid crystal display according to claim 44, wherein the adsorption molecule having the characteristic group expressed by the chemical formula (2-1) and the —O—Si bond group at the molecular end group is a compound expressed by the following chemical formula (2-2):

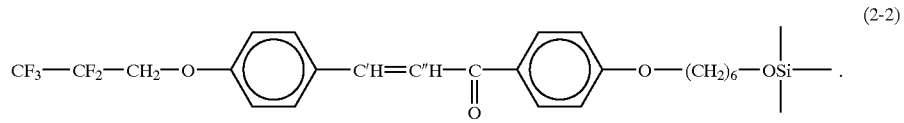

46. The liquid crystal display according to claim 44, wherein a pretilt angle and/or a pretilt orientation of the adsorption molecules accommodated in the cell gap are controlled by tilt and/or orientation of alignment of the adsorption molecules' major axes with respect to surface of the substrate.

47. The liquid crystal display according to claim 44, wherein the adsorption molecules forming the liquid crystal alignment film are cross-linked to each other via a boning line(s) of C' and/or C" in the chemical formula (2-1) or (2-2).

48. The liquid crystal display according to claim 44, wherein the liquid crystal alignment film has film thickness of 0.5 nm or more to less than 10 nm.

49. The liquid crystal display according to claim 44, wherein the liquid crystal alignment film is a thin film of a monomolecular layer form.

50. The liquid crystal display according to claim 44, wherein the liquid crystal alignment film comprises the aggregation of adsorption molecules of various kinds.

51. The liquid crystal display according to claim 50, wherein the liquid crystal alignment film is an alignment film that controls its liquid crystal alignment capabilities in such a manner that the liquid crystal molecules are aligned at a desired pretilt angle by changing a proportion of various kinds of adsorption molecules.

52. A producing method of a liquid crystal display having a liquid crystal alignment film comprising an aggregation of adsorption molecules directly bonded and anchored to or indirectly bonded and anchored to a surface of a substrate forming thereon electrodes through another material layer via chemical adsorption, the producing method comprising:
the process that chemical adsorption material having a characteristic group expressed by the following chemical formula (2-1) and a —O—Si bond group at a molecular end portion thereof is dissolved in non-water-borne solvent, to prepare chemical adsorption solution;
the process that the chemical adsorption solution is put into contact with the surface of the substrate forming the electrodes thereon, so that the chemical adsorption material in the chemical adsorption solution is chemically adsorbed on the surface of the substrate; and the solution draining and drying process that the surface of the substrate to which the chemical adsorption material was bonded is cleaned by use of the non-water-borne cleaning solvent and, thereafter, the substrate is stood up in a specific direction to cut and dry the cleaning solution:

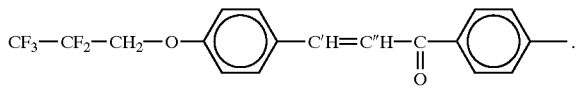

(2-1)

53. The producing method of the liquid crystal display according to claim 52, which further comprises the polarized ultraviolet irradiation process that after the solution draining and drying process, the adsorption molecules on the surface of the substrate are irradiated with polarized ultraviolet light, so that they are cross-linked to each other via a bonding line of a carbon-carbon double bond portion of the chemical formula (2-1).

54. The producing method of the liquid crystal display according to claim 52, wherein a series of alignment film treatment processes comprising the solution draining and the drying process and the polarized ultraviolet irradiation process are repeated a number of times in such a manner that the solution draining and drying process returns back again from the polarized ultraviolet irradiation process, and each time when repeated, the solution draining and drying direction is varied and that the polarized ultraviolet light irradiation region and polarized ultraviolet light irradiation direction, or the polarized ultraviolet light irradiation region and polarized ultraviolet light irradiation angle, or the polarized ultraviolet light irradiation region, polarized ultraviolet light irradiation direction and polarized ultraviolet light irradiation angle, are varied, whereby the adsorption molecules are varied in tilt of their major exes with respect to the surface of the substrate and/or in orientation of alignment thereof from one divided region to another of a number of divided regions into which a region corresponding to one picture element is divided in a pattern-like form.

55. The producing method of the liquid crystal display according to claim 52, wherein aprotic solvent is used as the non-water-borne solvent for use in cleaning, so that unreacted chemical adsorption material is cleaned and removed from the surface of the substrate by use of the aprotic solvent, to produce a thin film of a monomolecular layer form.

56. The producing method of the liquid crystal display according to claim 52, wherein a mixed solvent of aprotic solvent and protic solvent is used as the non-water-borne solvent for use in cleaning, so that unreacted chemical adsorption material is cleaned and removed from the surface of the substrate by use of the mixed solvent, to produce a thin film of a monomolecular layer form.

57. The producing method of the liquid crystal display according to claim 52, wherein the chemical adsorption material having a characteristic group expressed by the chemical formula (2-1) and a —O—Si bond group at a molecular end portion thereof is a compound expressed by the following chemical formula (2-2):

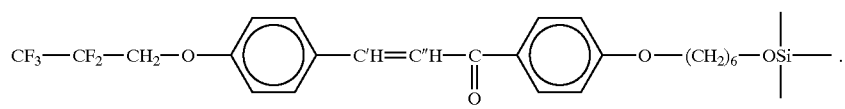

(2-2)

* * * * *

UNITED STATES PATENT AND TRADEMARK OFFICE
CERTIFICATE OF CORRECTION

PATENT NO.    : 6,524,715 B1
DATED         : February 25, 2003
INVENTOR(S)   : Tadashi Ootake et al.

It is certified that error appears in the above-identified patent and that said Letters Patent is hereby corrected as shown below:

<u>Title page,</u>
Item [57], ABSTRACT,
Lines 1 and 5, change "absorption" to -- adsorption --;
Line 10, change "absorbed" to -- adsorbed --.

<u>Column 10,</u>
Line 1, change "exes" to -- axes --.

<u>Column 11,</u>
Line 53, change "exes" to -- axes --.

<u>Column 16,</u>
Line 57, change "exes" to -- axes --.

<u>Column 36,</u>
Line 9, change "exes" to -- axes --.

<u>Column 37,</u>
Line 38, change "exes" to -- axes --.

<u>Column 38,</u>
Line 41, change "exes" to -- axes --.

<u>Column 39,</u>
Line 63, change "exes" to -- axes --.

<u>Column 44,</u>
Line 7, change "exes" to -- axes --.

Signed and Sealed this

Fifteenth Day of July, 2003

JAMES E. ROGAN
*Director of the United States Patent and Trademark Office*